United States Patent [19]
Cassels et al.

[11] Patent Number: 6,004,998
[45] Date of Patent: Dec. 21, 1999

[54] FLAVONOID AND BIFLAVONOID DERIVATIVES, THEIR PHARMACEUTICAL COMPOSITIONS, THEIR ANXIOLYTIC ACTIVITY

[75] Inventors: Bruce Kennedy Cassels, Casilla, Chile; Federico Jose Dajas, Montevideo, Uruguay; Jorge Horacio Medina; Alejandro Constantino Paladini, both of Buenos Aires, Argentina; Rodolfo Horacio Silveira, Montevideo, Uruguay

[73] Assignee: University of Strathclyde, United Kingdom

[21] Appl. No.: 08/939,975

[22] Filed: Sep. 29, 1997

Related U.S. Application Data

[62] Division of application No. 08/586,796, filed as application No. PCT/GB94/01803, Aug. 17, 1994, Pat. No. 5,756,538.

[30] Foreign Application Priority Data

Aug. 17, 1993 [GB] United Kingdom .................... 9317071

[51] Int. Cl.$^6$ ........................ A61K 31/35; C07D 311/28; C07D 311/30; C07D 311/32
[52] U.S. Cl. .......................... 514/456; 549/400; 549/402; 549/403
[58] Field of Search .................................... 549/403, 400, 549/402; 514/456

[56] References Cited

U.S. PATENT DOCUMENTS 3,903,266  9/1975  Robbins .................................. 424/183
4,241,069  12/1980  Buckler et al. .......................... 424/263

FOREIGN PATENT DOCUMENTS 0 558 245 A1  9/1993  European Pat. Off. ..

OTHER PUBLICATIONS

Chen et al. (CA 107:236283), 1987.
Guidugli et al. (CA 102:5497), 1985.
J.H. Medina et al; Chrysin (5,7–Di–Oh–Flavone), A Naturally–Occuring Ligand For Benzodiazepine Receptors, With Anticonvulsant Properties, *Biochemical Pharmacology*, 40 No. 10, pp. 2227–2231 (1990).
M. Nielsen et al; High Affinity Of The Naturally–Occurring Biflavonoid, Amentoflavon, To Brain Benzodiazepine Receptors In Vitro, *Biochemical Phamacology*, 37, No. 17, pp. 3285–3287 (1988).
B.K. Chakravarthy et al; Isolation of Amentoflavone from Selaginella rupestris and its Pharmacological activity on Central Nervous System, Smooth Muscles and Isolated Frog Heart Preparations; *Planta Medica* 43, pp. 64–70 (1981).
K. Hayashi et al; Mechanism of Action of the Antiherpesvirus Biflavone Ginkgetin, *Antimicrobial Agents and Chemotherapy*, 36 No. 9, pp. 1890–1893 (1992).
R.K. Goel et al; Mechanism of anti–ulcerogenic effect of amentoflavone, *Indian J. Med. Res* 88, pp. 192–196 (1988).
G. Spedding et al; Inhibition of reverse transcriptases by flavonoids, *Antiviral Research* 12, pp. 99–110 (1989).
M.R. Cholbi et al; Inhibitory effects of phenolic compounds on $CCl_4$–induced microsomal lipid peroxidation, *Experientia* 47, pp. 195–199 (1991).
K.H. Shin et al; Sedative Action of Spinosin, *Arch. Pharm. Res.* 1 (1), pp. 7–11 (1978).
Batchelor et al. (CA 102:24352), 1985.
Edwards et al. (CA 91:13471), 1979.
He et al. (CA 111:7098), 1989.
Batchelor et al. (CA 92:128727), 1980.
Sasaki et al. (CA 72:26333) 1970.
Kinoshita et al. (CA 114:101428) 1991.
Singh et al. (CA 113:114871) 1990.
He et al. (CA 113:6095) 1990.
Thakar et al. (CA 100:121000) 1984.
Cutroneo et al. (CA 77:13948) 1972.
Lakshmi et al. (CA 77:5287) 1972.
Covello et al. (CA 74:99795) 1971.
Prakash et al. (CA 114:101416) 1991.
Hoshino et al. (CA 98:71744) 1983.
Reddy et al. (CA 94:83887) 1981.
Letcher (CA 113:23428) 1990.
Sangwan et al. (CA 101:23175) 1984.
Looker et al. (CA 100:85455) 1984.
Metzner et al. (CA 98:83243) 1983.
Covello et al. (CA 84:112062) 1976.
Reichel et al. (CA 83:96949) 1975.
Dhar et al. (CA 83:42478) 1975.
Pownall (CA 81:48936) 1974.

*Primary Examiner*—Laura L. Stockton
*Attorney, Agent, or Firm*—Alston & Bird LLP

[57] ABSTRACT

Certain flavonoids, notably derivatives of flavone, chrysin and apigenin, together with dimers thereof such as amentoflavone, have been found to possess anxiolytic properties (i.e., anxiety reducing properties) without exhibiting a sedative effect. Novel compounds and pharmaceutical formulations are also described.

3 Claims, 19 Drawing Sheets

FLAVONOID AND BIFLAVONOID DERIVATIVES, THEIR PHARMACEUTICAL COMPOSITIONS, THEIR ANXIOLYTIC ACTIVITY

This application is a divisional of application Ser. No. 08/586,796, filed May 31, 1996 now U.S. Pat. No. 5,756,538.

FIELD OF THE INVENTION

The present invention relates to certain flavonoids which have been found to have anxiolytic properties (i.e. anxiety reducing) without corresponding depression of the central nervous system which is commonly also found in known sedatives such as benzodiazepines.

BACKGROUND OF THE INVENTION

Some compounds of the invention are novel; other compounds are known but no pharmaceutical uses have previously been described.

Flavone is a known compound which is described in the Merck Index (entry 4030). Chrysin (2261) and apigenin (763) are other known flavonoids. Chrysin has been described as having binding properties for benzodiazepine receptors and anticonvulsant properties in Medina J. H. et al. Biochem. Pharmacol; 40: 2227–2232, 1990. This reference also suggests that chrysin may possess myorelaxant (i.e. muscle relaxant) action.

Flavone, 2-phenyl-4H-1-benzopyran-4-one has the formula

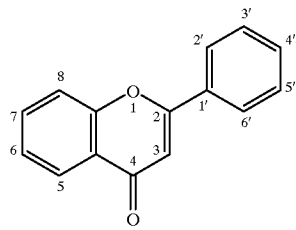

Chrysin is 5,7-dihydroxyflavone
Apigenin is 4', 5,7-trihydroxyflavone.

SUMMARY OF THE INVENTION

The present invention relates to a method of treatment of anxiety in a patient which comprises administering to the patient an effective non-toxic amount of a flavonoid compound of general formula (I):

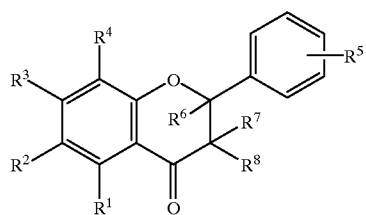

(I)

where $R^1$, $R^2$, $R^3$ and $R^4$, $R^5$ and $R^8$ are independently selected from H, OH, R, $NO_2$, halo, OR, $NH_2$, NHR, $NR_2$, COOR, COOH, CN, or a sugar group;

$R^6$ and $R^7$ are both H, or $R^6$ and $R^7$ together form a single bond;

R is $C_{1-6}$ alkyl or alkenyl;

or the administration of an effective non-toxic amount of a biflavonoid which is a dimer of a compound of general formula (I) and wherein $R^1$ to $R^8$ and R have the meanings given for general formula (I).

It is found that the compounds of the present invention have anxiolytic properties without the associated depression of the central nervous system (e.g. sedative and muscle relaxant effects) commonly found with benzodiazedines. This may allow patients to be treated for anxiety without inducing sedative or myorelaxant side-effects.

It is found further that compounds of the present invention may not show an anti-convulsant activity commonly found with benzodiazepines.

DETAILED DESCRIPTION OF THE INVENTION

Figure 1:
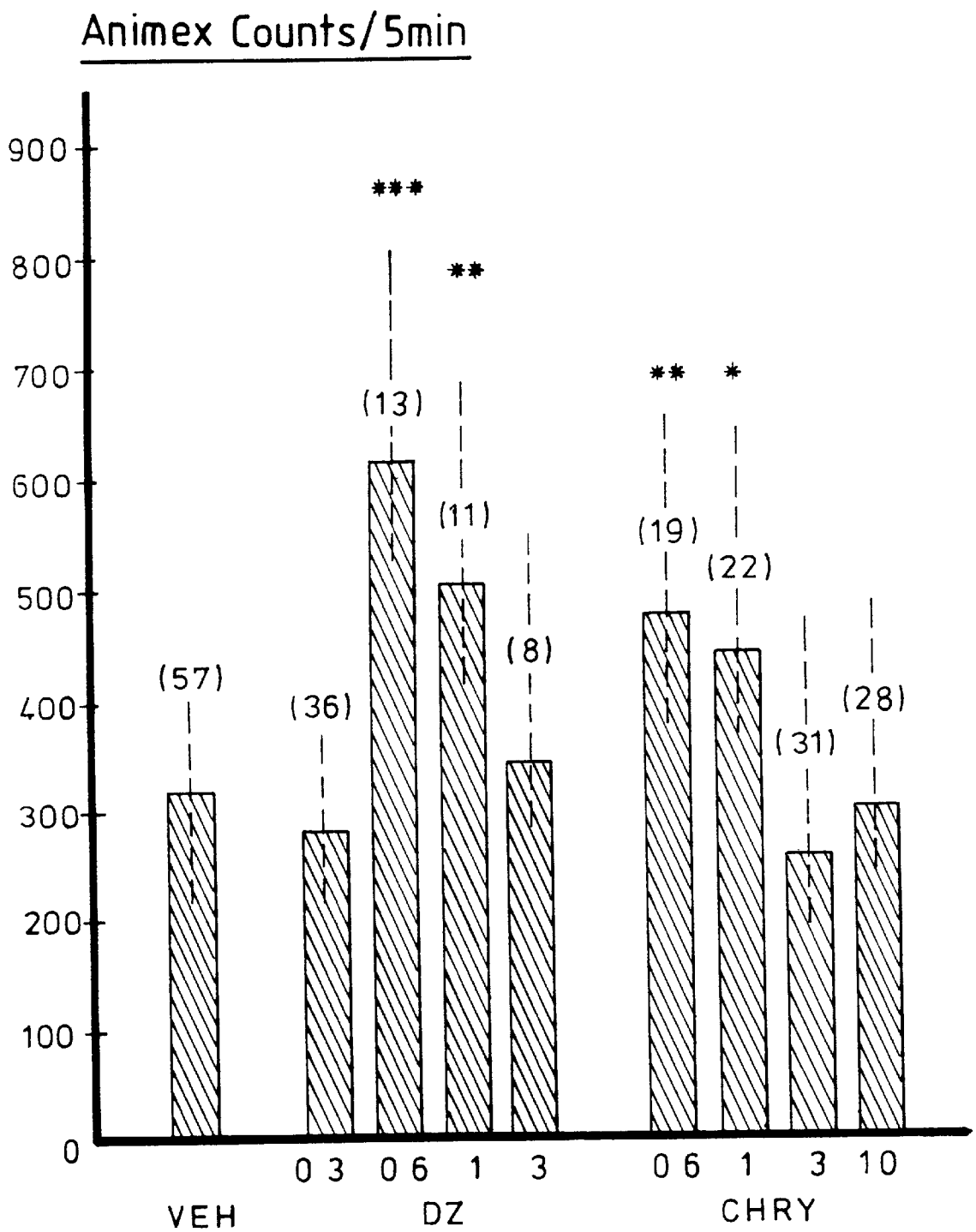
FIG. 1 is a graph illustrating ambulatory locomotor activity counts in mice during a five minute test session, twenty minutes after intraperitoneal (i.p.) injection with diazepam (DZ) or chrysin (CHRY)

The compounds of general formula (I) wherein $R^1$, $R^2$, $R^3$, $R^4$ and $R^5$ may independently be H, OH or halo (including F, Cl, Br or I) are preferred. The preferred halo substituent is Br, F or Cl.

The following compounds of general formula (I) are particularly preferred wherein $R^1$, $R^3$, and $R^5$ may be hydroxy. Also wherein $R^1$, and $R^3$ are hydroxy and $R^5$ is halo. Alternatively wherein $R^3$ is hydroxy and $R^1$ is hydrogen, or wherein $R^3$ and $R^1$ are both hydroxy is preferred. More preferably $R^2$ and $R^4$ are both halo. More preferably $R^5$ is OH or halo.

When $R^5$ is halo it is particularly preferred that the compounds of general formula (I) are substituted at the 2' position.

The compounds of general formula (I) which are flavone, chrysin, apigenin and the derivatives 2'-chlorochrysin, 2'-fluorochrysin, 6,8-dibromochrysin and 7-bromoflavone are particularly preferred.

Compounds where $R^6$ and $R^7$ together form a single bond are flavone derivatives, whereas compounds where $R^6$ and $R^7$ are both H are flavonone derivatives.

The sugar group may be any of the known sugars, including monosaccharides, disaccharides and polysaccharides; and may in particular be glycosyl, galactopyranosyl or mannopyranosyl.

The biflavonoid is a dimer of two covalently bonded moieties which are each of general formula (I) as set out above. Bonding between the two moieties generally occurs at the 3'-position of one moiety and the 8-position of the other moiety. The preferred biflavonoid has general formula (II) wherein $R^1$ to $R^8$ and R have the same meanings as for general formula (I).

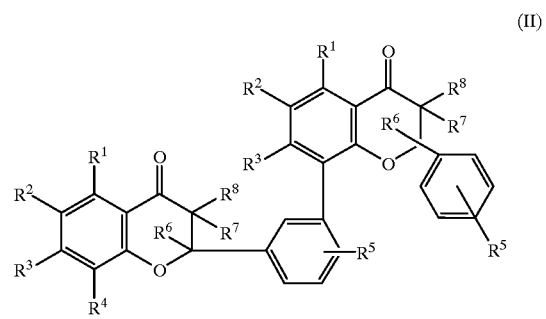

(II)

The compounds of general formula (II) wherein $R^1$, $R^3$ and $R_5$ in each of the dimer moieties of general formula (I) are hydroxy or methoxy are preferred.

The compounds of general formula (II) wherein the compounds are amentoflavone, ginkgetin or isoginkgetin are preferred.

Pharmaceutical formulations include at least one compound of general formula (I) or (II) together with at least one pharmaceutically acceptable carrier or excipient. Each carrier must be "pharmaceutically acceptable" in the sense of being compatible with the other ingredients of the formulation and not injurious to the patient.

It should be understood that the flavonoid compounds of the present invention can be administered in the form of pharmaceutically acceptable salts or esters thereof. Salts are usually acid addition salts (e.g. with hydrohalogen acids) or acceptable metal salts (e.g. Na, Ca, Mg).

Formulations include those adapted for oral, rectal, nasal, vaginal and parenteral (including subcutaneous, intramuscular, intravenous and intradermal) administration. The formulations may conveniently be presented in unit dosage form and may be prepared by any methods well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then if necessary shaping the product.

Formulations of the present invention adapted for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethylcellulose), lubricant, inert diluent, preservative, disintegrant (e.g. sodium starch glycollate, cross-linked povidone, cross-linked sodium carboxymethylcellulose) surface-active or dispersing agent. Moulded tablets may be made by moulding in a suitable machine a mixture of the powdered compound moistened with an inert liquid diluent. The tablets may optionally be coated or scored and may be formulated so as to provide controlled release of the active ingredient therein using, for example, hydroxypropylmethylcellulose in varying proportions to provide the desired release profile.

Formulations for rectal administration may be presented as a suppository with a suitable base comprising for example cocoa butter or a salicylate.

Formulation for vaginal administration may be presented as pessaries, tampons, creams, gels, pastes, foams or spray formulations containing in addition to the active ingredient such carriers as are known in the art to be appropriate.

Formulations for parenteral administration include aqueous and non-aqueous isotonic sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

The dose will depend on a number of factors known to the skilled physician including the severity of the conditions, the identity of the recipient; and also the efficacy and toxicity of the particular compound of general formula (I) which is being administered. Generally doses in the range 0.1–100 mg/kg body weight may be used, particularly 1–10 mg/kg. The frequency of administration will vary depending on the rate of metabolism or excretion of the administered compound, but may be repeated daily, optionally as two or more sub-doses. Unit doses of 20 to 500 mg, preferably 100 to 400 mg may be used.

The present invention further relates to a flavonoid compound of general formula (I)

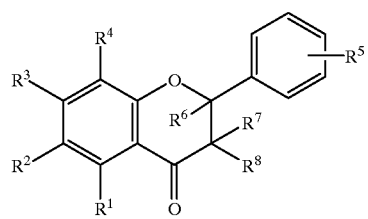

(I)

wherein $R^1$, $R^2$, $R^3$, $R^4$, $R^5$ and $R^8$ are independently selected from H, OH and halo.

$R^6$ and $R^7$ are both H, or $R^6$ and $R_7$ together form a single bond; and

R is $C_{1-6}$ alkyl or alkenyl.

Embodiments of the invention will now be described by way of example only.

EXAMPLE 1 (Preparation of synthetic flavonoids)

1. Preparation of Halogenated Chrysin

2'-fluorochrysin and 2'-chlorochrysin were prepared by the Floc'h Lefeuvre synthesis (Tetrahedron Lett. 27, 5503–5504, 1985) by reaction of ortho-fluoro or chlorobenzoyl chlorides with the ylid obtained from 2,4,6-trihydroxyphenacylidene-triphenylphosphorane. Other compounds including 6,8 dibromo chrysin were prepared from chrysin using the classical Allan-Robinson synthetic route (J. Allan and R. Robinson (1924) J. Chem. Soc. p2192).

2. Preparation of 7-bromo flavone

Bromine was added to a solution of flavanone in carbon tetrachloride at 0° C. The ratio of bromine/flavanone was 1.3 in molar terms. The temperature of the solution was raised to 30° C. and kept there for 1 hour. The temperature of the solution was then raised to 65° C. and kept there for 45 minutes.

The reaction mixture was then extracted with an equal volume of a saturated solution of sodium metabisulphite and then dried with anhydrous sodium sulphate. The product was then recovered by evaporation of the solvent.

Figure 19:
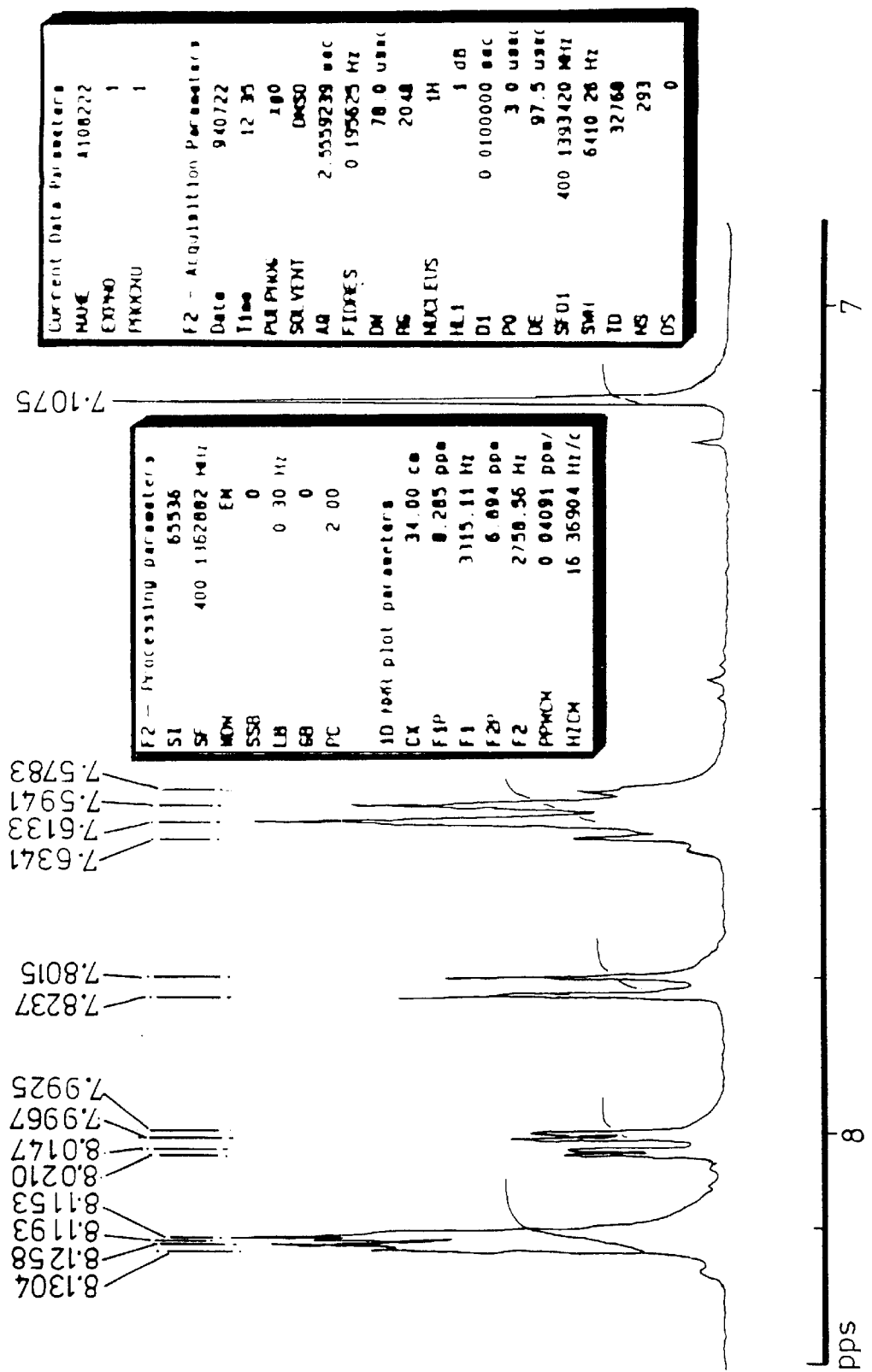
FIG. 19 is a graph illustrating the results of NMR analysis of a mixture of brominated flavones and identifying 7-bromoflavon as an active ingredient.

This gave a mixture of brominated flavones, in which the only active ingredient was identified by NMR analysis as 7-bromo flavone (as shown in FIG. 19).

EXAMPLE 2 (Experimental effect of flavonoids)

Animals

Male CF1 mice from our breeding stock weighing 28–35 g were used. The animals were placed in groups of 10–12 with free access to water and food, and maintained on a 12 h/12 h day-night cycle.

Drugs:

Diazepam (DZ; Hoffmann-La Roche) and the flavonoids were dissolved in DMSO 40%, NaOH 0.1N (7:3: v/v) at pH 8.2 Control animals were injected with the same vehicle (VEH). RO 15-1788 (Hoffmann-La Roche) was suspended in DMSO 10%, propyleneglycol 10% in distilled water.

Experimental Devices (a) Elevated Plus Maze: consisted of 4 perpendicularly disposed wood arms (20×5 cm; two had 35 cm high wood walls, and two were open) linked by a central 10×10 cm square. The maze was suspended 50 cm from the room floor. Animals were placed on the central part of the maze facing a closed arm. This test has been widely validated to measure anxiety in rodents. The number of entries into and the time spent in the open and closed arms were counted during 5 min. A selective increase in the parameters corresponding to open arms reveals an anxiolytic effect. Total exploratory activity (number of entries in both arms) was also determined.

(b) Holeboard Test: consisted of a wood box (60×60×30 cm) with four 2 cm diameter holes equidistant in the floor. The number of head-dips and the time spent head-dipping were counted during 5 min. An increase in the number and the time spent head-dipping implies a greater exploratory activity. A decrease of both parameters reveals a sedative behavior.

(c) Locomotor Activity Test: we used an OPTO-VARIMEX apparatus consisting of a glass box (36×15×20 cm) and two lateral bars with 15 light beams (0.32 cm diameter, beam spacing 2.65 cm). The apparatus detects automatically all the mouse movements, and discriminates between total and ambulatory activity. The locomotor activity (number of movements across the beams) was counted during 5 min. An increase in the number of transitions through the beams reflects an augmented locomotor activity.

(d) Horizontal Wire Test: It consisted of an horizontally strung wire (1 mm diameter, 15 cm long), placed at 20 cm from the table. Mice were lifted by the tail, allowed to grasp the wire with their forepaws and released. The number of mice that did not grasp the wire with their forepaws or actively grasped the wire with at least one hindpaw within 3 sec was determined. After two trials, Performed at 5 min.

intervals, the test took place. A myorelaxant drug, like diazepam at high doses, will impair the ability of mice to grasp the wire. Generally, this state of muscle relaxation is commonly associated with sedation.

General Experimental Procedure

The General procedure for all the tests is as follows: mice were injected with vehicle or the drug solution 20 min before beginning of the test and put into another home cage. Ro 15-1788, a specific BZD receptor antagonist was injected 10 min before the tested drug. All the injections were given intraperitoneally (i.p.). Control mice were tested in each session, in parallel with those animals receiving the test drug or diazepam. Testing was carried out 'blind'. All data were submitted to analysis of variance (ANOVA). Post-hoc comparisons between individual treatments and controls were made using Dunnett's t-test.

Results

The results of experiments in devices (a) to (d) are summarised in the FIGS. 1–18.

FIG. 1 shows ambulatory locomotor activity counts during a 5 min test session in an OPTO-Varimex apparatus, 20 min after IP injection with DZ (0.3–3 mg/kg), or chrysin (CHRY, 0.6–10 mg/kg). Data are expressed as medians (interquartile range) of (n) number of animals. *p<0.05, p<0.02, *p<0.002 significantly different from controls (Mann Whitney test).

Figure 2:
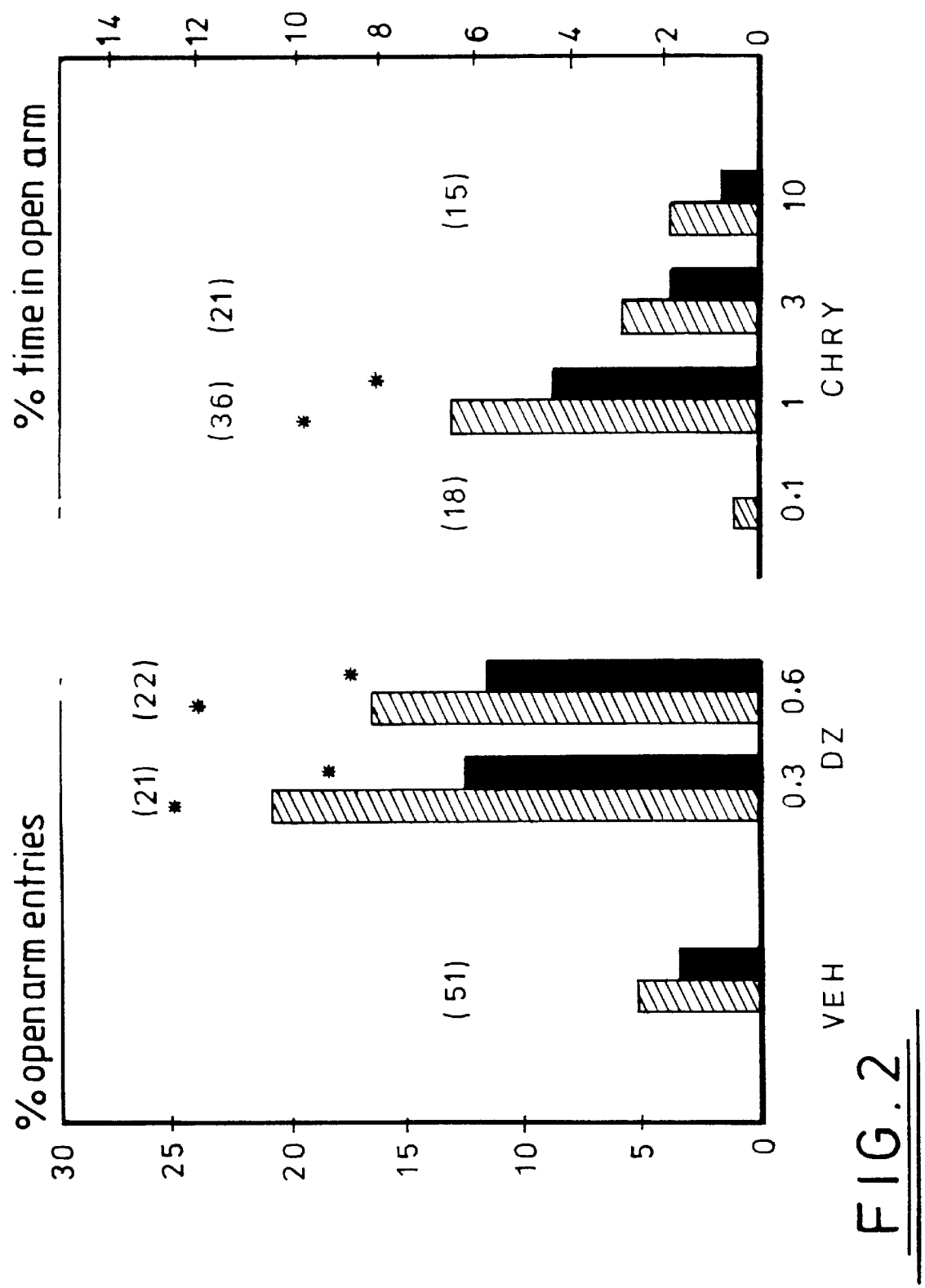
FIG. 2 is a graph illustrating test results of mice given a five minute test in the elevated plus-maze, twenty minutes after i.p. injection with DZ or CHRY.

FIG. 2 shows mean (±S.E.M.) percentage of open arm entries (hatched bars) and percentage of time (sec) spent in the open arms (closed bars) in mice given a 5 min test in the elevated plus-maze, 20 min after i.p. injection with DZ (0.3 and 0.6 mg/kg), or CHRY (0.1–10 mg/kg). *p<0.01, significantly different from controls (two-tailed Dunnett's t-test after analysis of variance).

Figure 3:
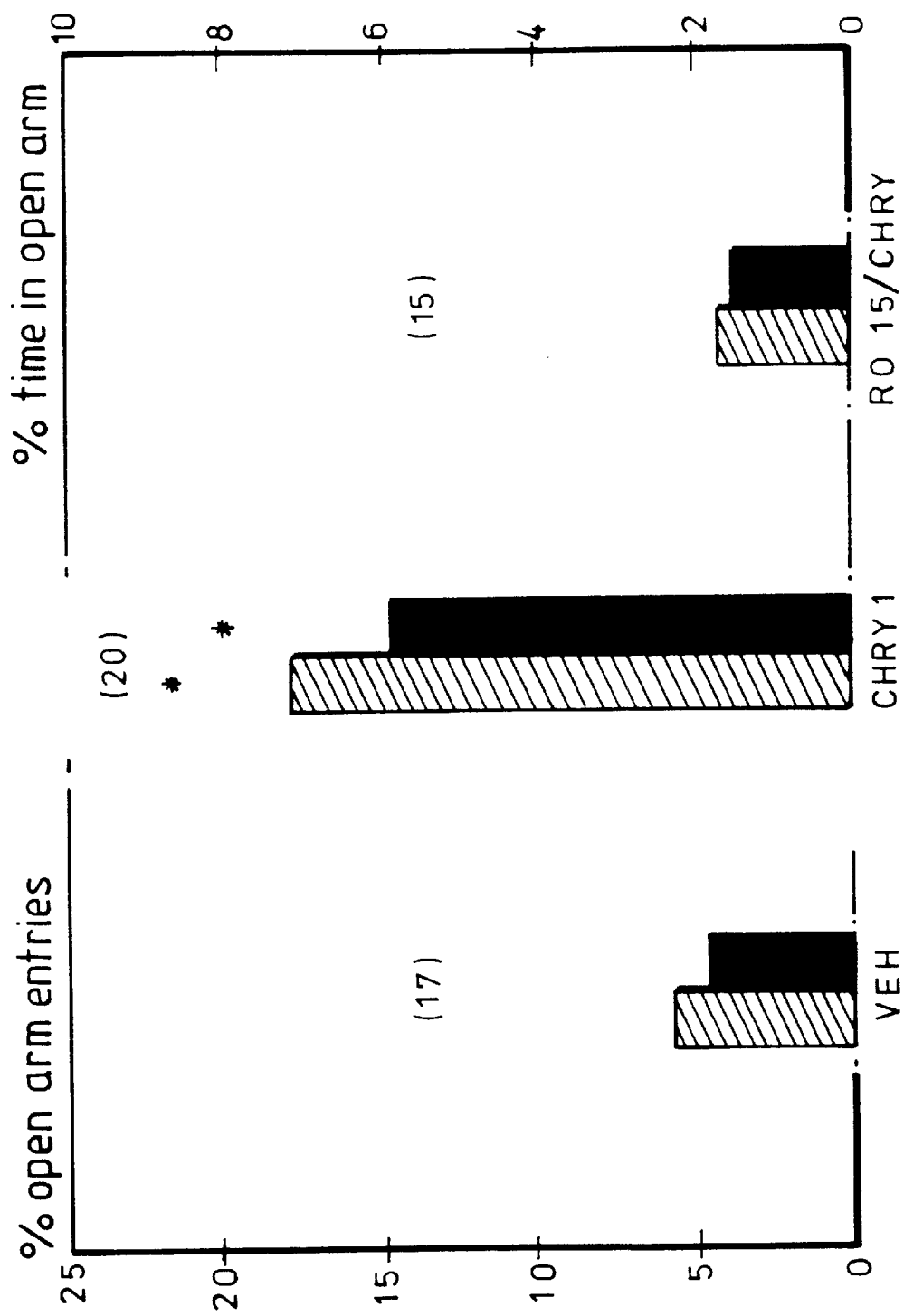
FIG. 3 is a graph illustrating test results of mice given a five minute test in the elevated plus-maze, twenty minutes after i.p. injection with vehicle (VEH), CHRY or CHRY plus RO 15-1788 administered ten minutes before chrysin.

FIG. 3 shows mean (±S.E.M.) percentage of open arm entries (hatched bars) and percentage of time (sec) spent in the open arms (closed bars) in mice given a 5 min test in the elevated plus-maze, 20 min after i.p. injection with VEH, CHRY (1 mg/kg) or CHRY+RO 15-1788 (3 mg/kg) administered i.p. 10 min before chrysin. * p<0.01, significantly different from controls (two-tailed Dunnett's t-test after analysis of variance). No significant differences were found in the total arm entries (F (2,49)=3.18).

Figure 4:
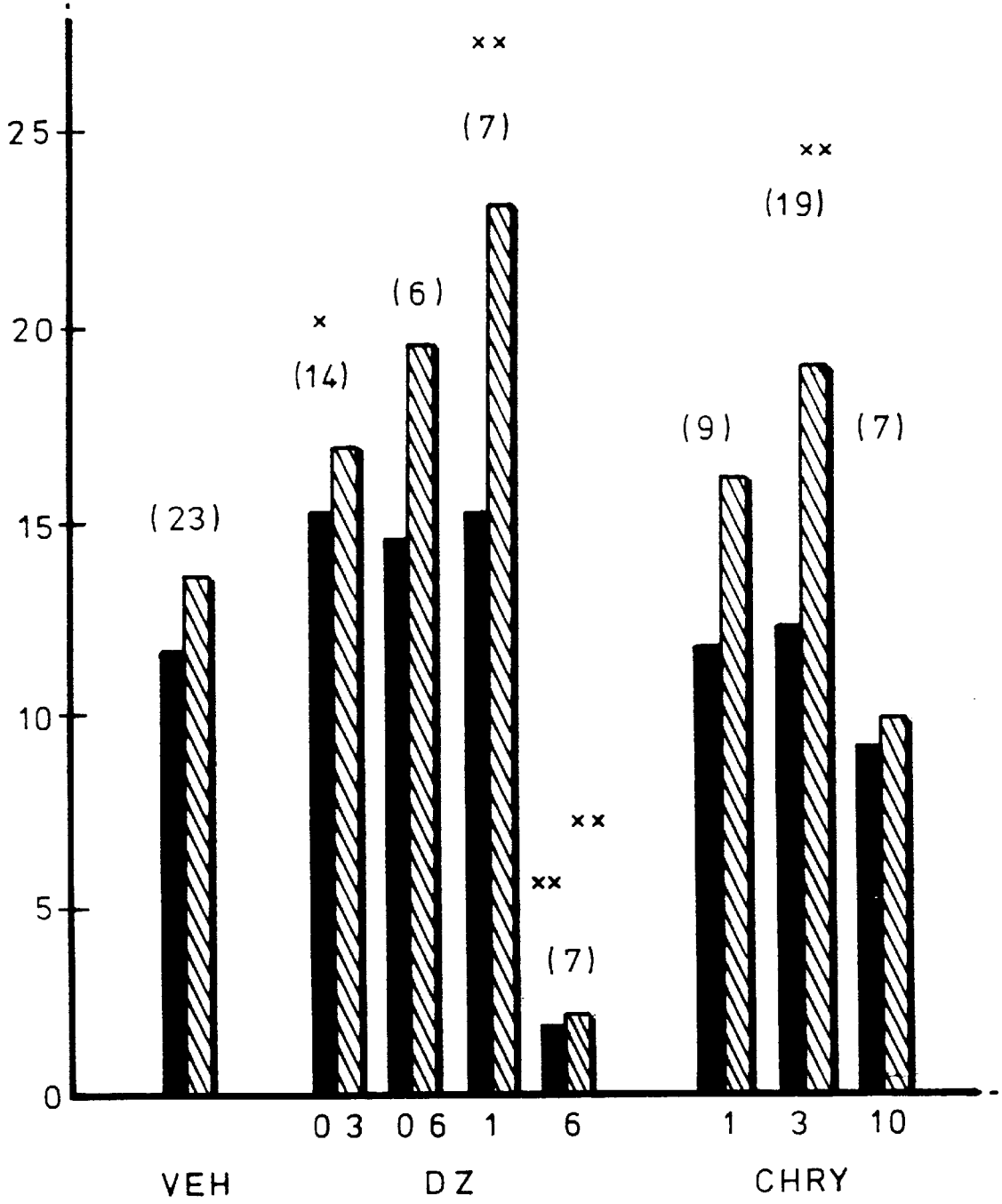
FIG. 4 is a graph illustrating the test results of mice given a five minute test in a holeboard, twenty minutes after i.p. injection with Z or CHRY.

FIG. 4 shows mean (±S.E.M.) number of head-dips (closed bars) and time (sec) spent head-dipping (hatched bars) for mice given a 5 min test in the holeboard, 20 min after an i.p. injection with DZ (0.3–6 mg/kg) or CHRY (1–10 mg/kg). *p<0.05, **p<0.01, significantly different from controls (two-tailed Dunnett's t-test after analysis of variance).

Figure 5:
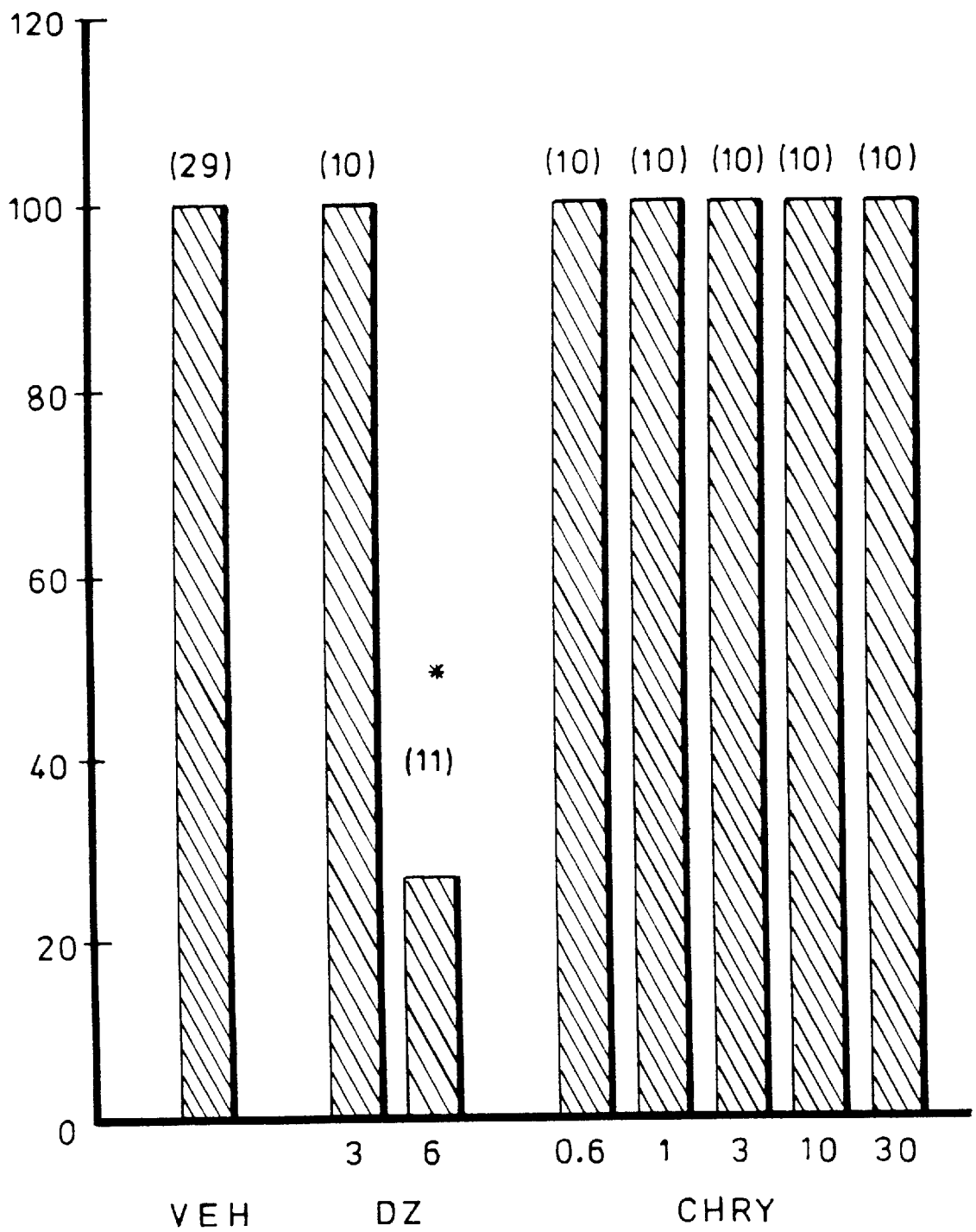
FIG. 5 is a graph illustrating test results of mice in a wire test, twenty minutes after i.p. injection with DZ or CHRY.

FIG. 5 shows the performance of mice in the wire test 20 min after an i.p. injection with DZ (3 and 6 mg/kg) or CHRY (0.6–30 mg/kg). The test took place after two trials, executed after a 5 min interval.

Figure 6:
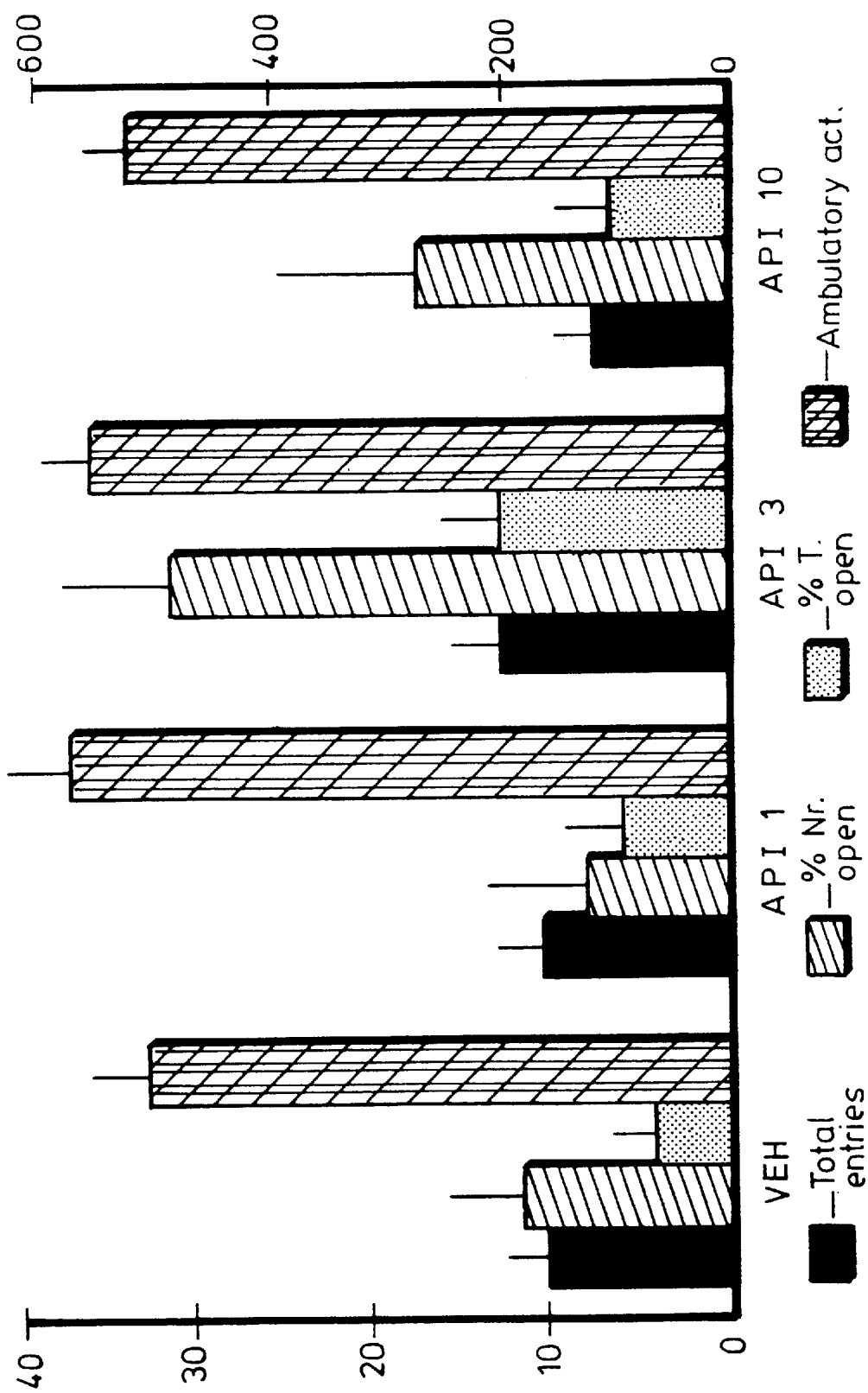
FIG. 6 is a graph illustrating test results of mice given a five minute test in the elevated plus-maze and ambulatory activity in mice given a five minute test, twenty minutes after i.p. injection with vehicle and apigenin.

FIG. 6 shows mean (±S.E.M.) of total entries, percentage of open arm entries (% Nr open) and percentage of time (sec) spent in the open arms (% T open) in mice given a 5 min test in the elevated plus-maze, and ambulatory activity in mice given a 5 min test in an OPTO-VARIMEX apparatus, 20 min after i.p. injection with vehicle and apigenin (1, 3, 10 mg/kg).

Figure 7:
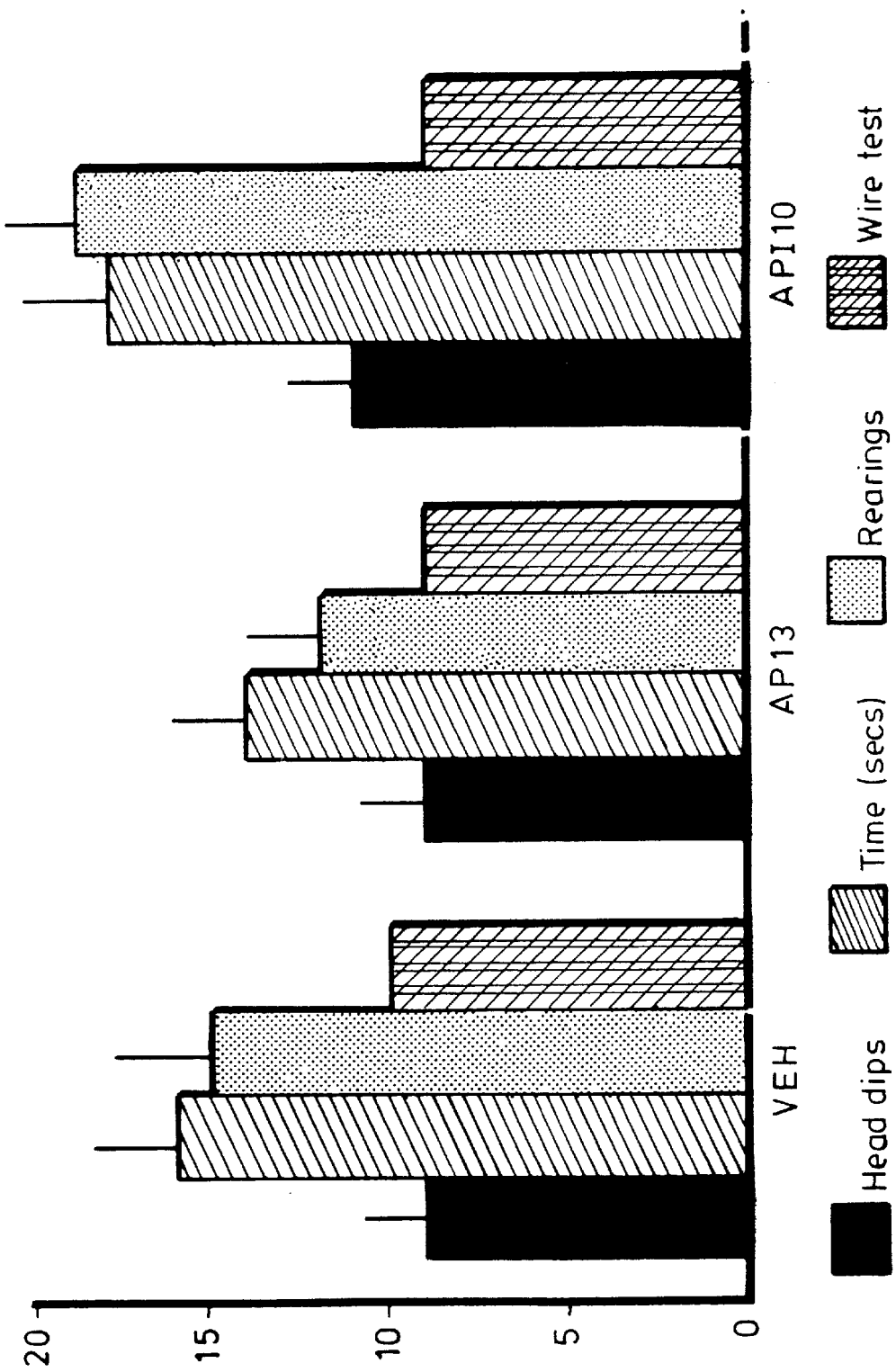
FIG. 7 is a graph illustrating test results of mice given a five minute test in the holeboard, and performance to grasping the wire test, twenty minutes after i.p. injection with vehicle and apigenin.
Figure 8:
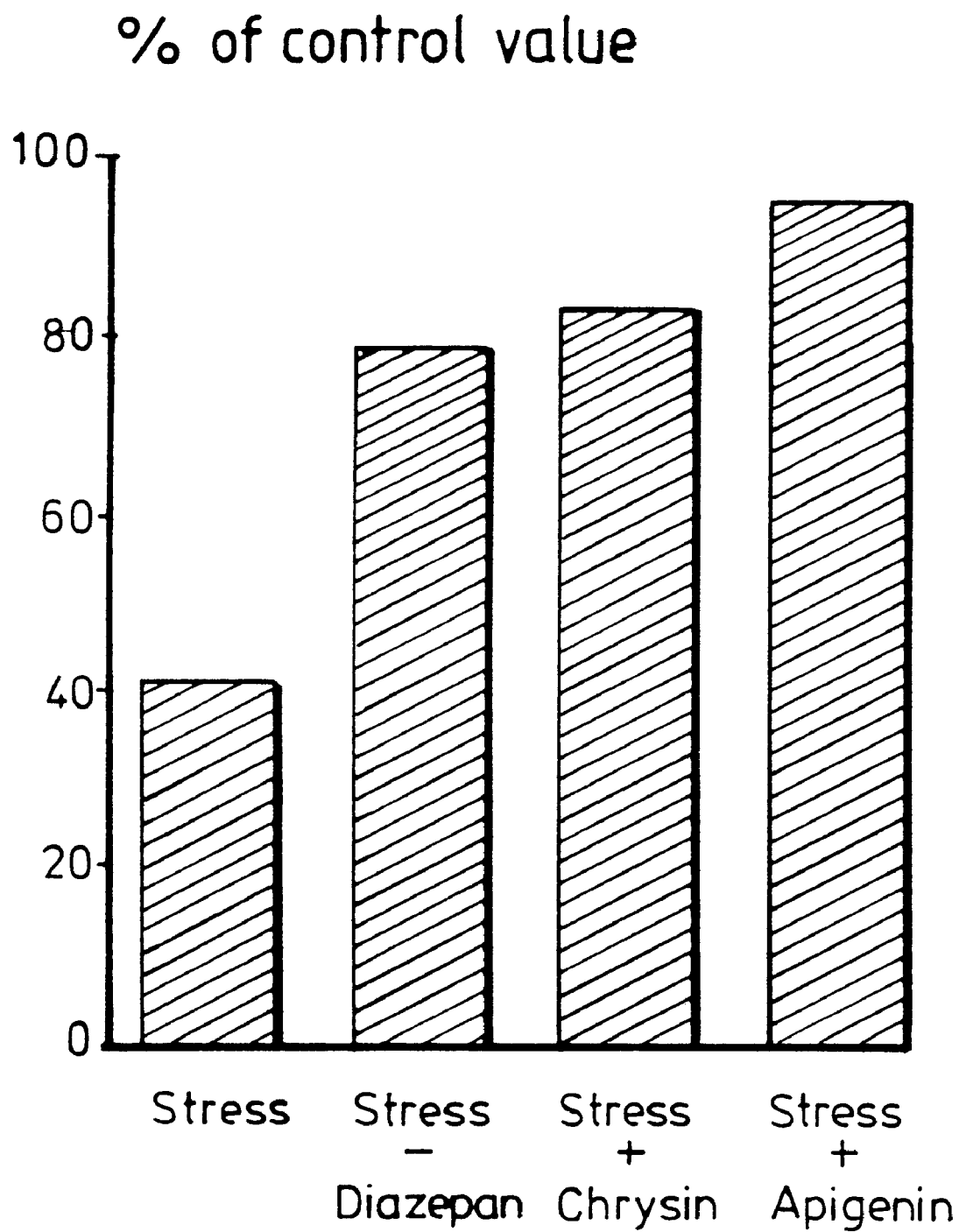
FIG. 8 is a graph illustrating noradrenaline levels in locus coeruleus nucleus after a session of immobilization stress alone or with pre-treatments.

FIG. 7 shows mean (±S.E.M.) number of head-dips and time (sec) spent head-dipping and rearings for mice given a 5 min test in the holeboard, and performance to grasping the wire test, 20 min after an i.p. injection with vehicle and apigenin 3 and 10 mg/kg; and FIG. 8 shows noradrenaline levels in locus coeruleus nucleus after a session of immobilization stress alone or with pretreatments as indicated in the figure (noradrenaline is expressed as percent of control value) Apigenin blocked almost completely the noradrenaline decrease provoked by stress—first bar. (Chrysin was almost equipotent with diazepam).

Figure 9:
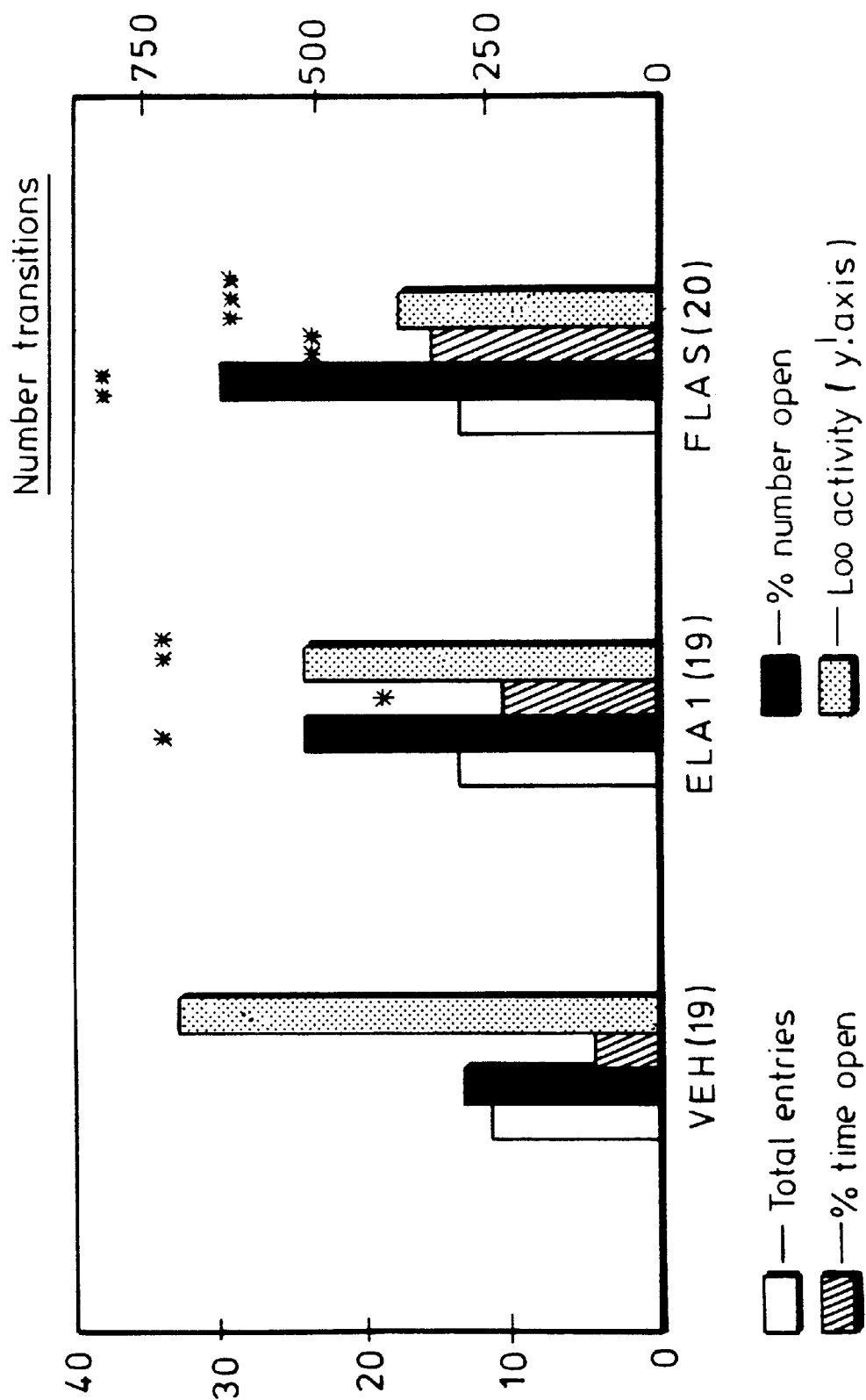
FIG. 9 is a graph illustrating test results of mice given a five minute test in the elevated plus-maze and ambulatory activity in mice given a five minute test, twenty minutes after i.p. injection with vehicle and flavone.

FIG. 9 shows total entries, percentage of open arm entries (% number open) and percentage of time (sec) spent in the open arms (% time open) in mice given a 5 min test in the elevated plus-maze, and ambulatory activity in mice given a 5 min test in an OPTO-VARIMEX apparatus, 20 min after i.p. injection with vehicle and flavone (1,3 mg/kg).

Figure 10:
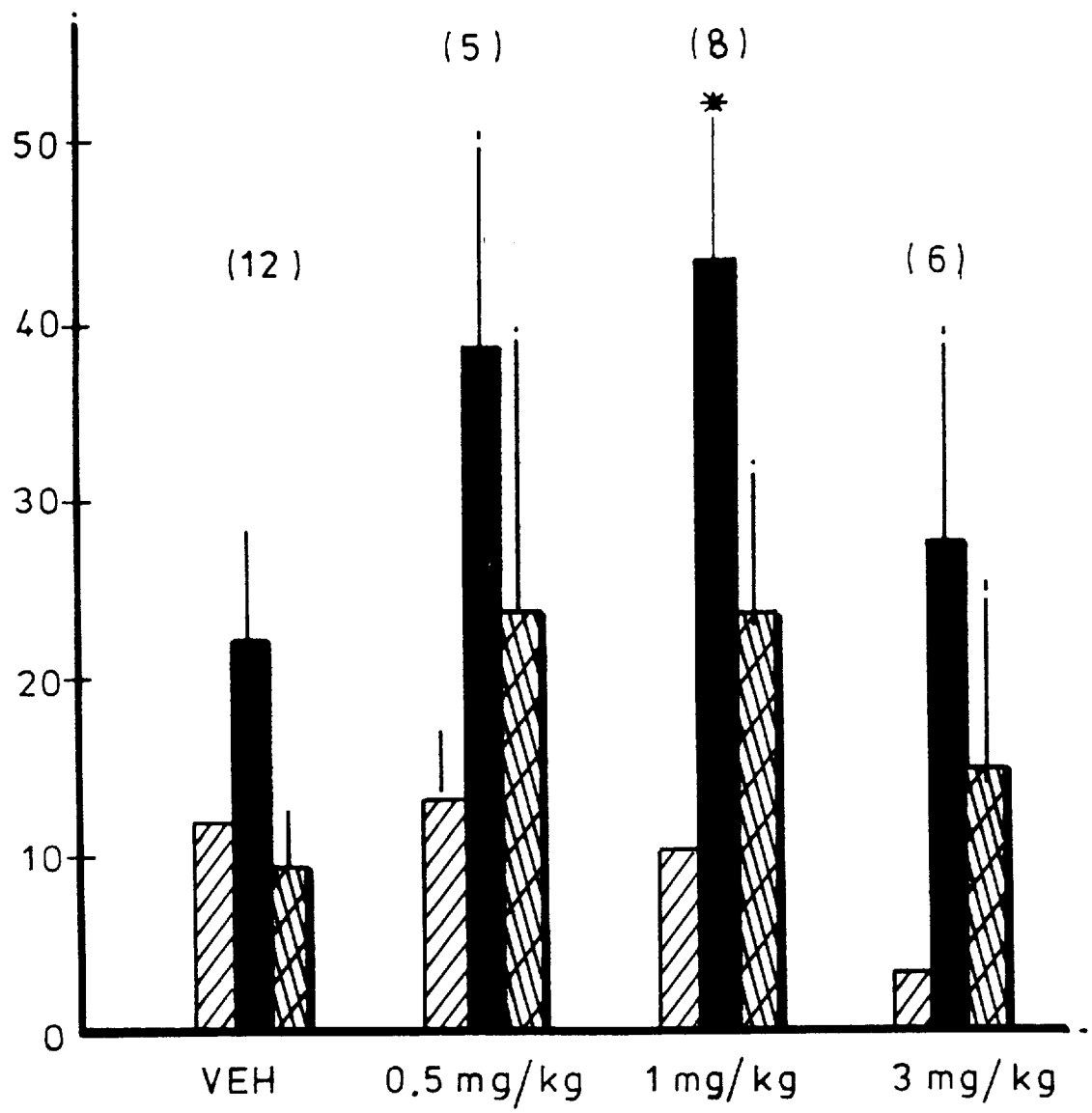
FIG. 10 is a graph illustrating test results of mice given a five minute test in the elevated plus-maze, twenty minutes after i.p. injection with vehicle and a mixture of brominated flavone.
Figure 11:
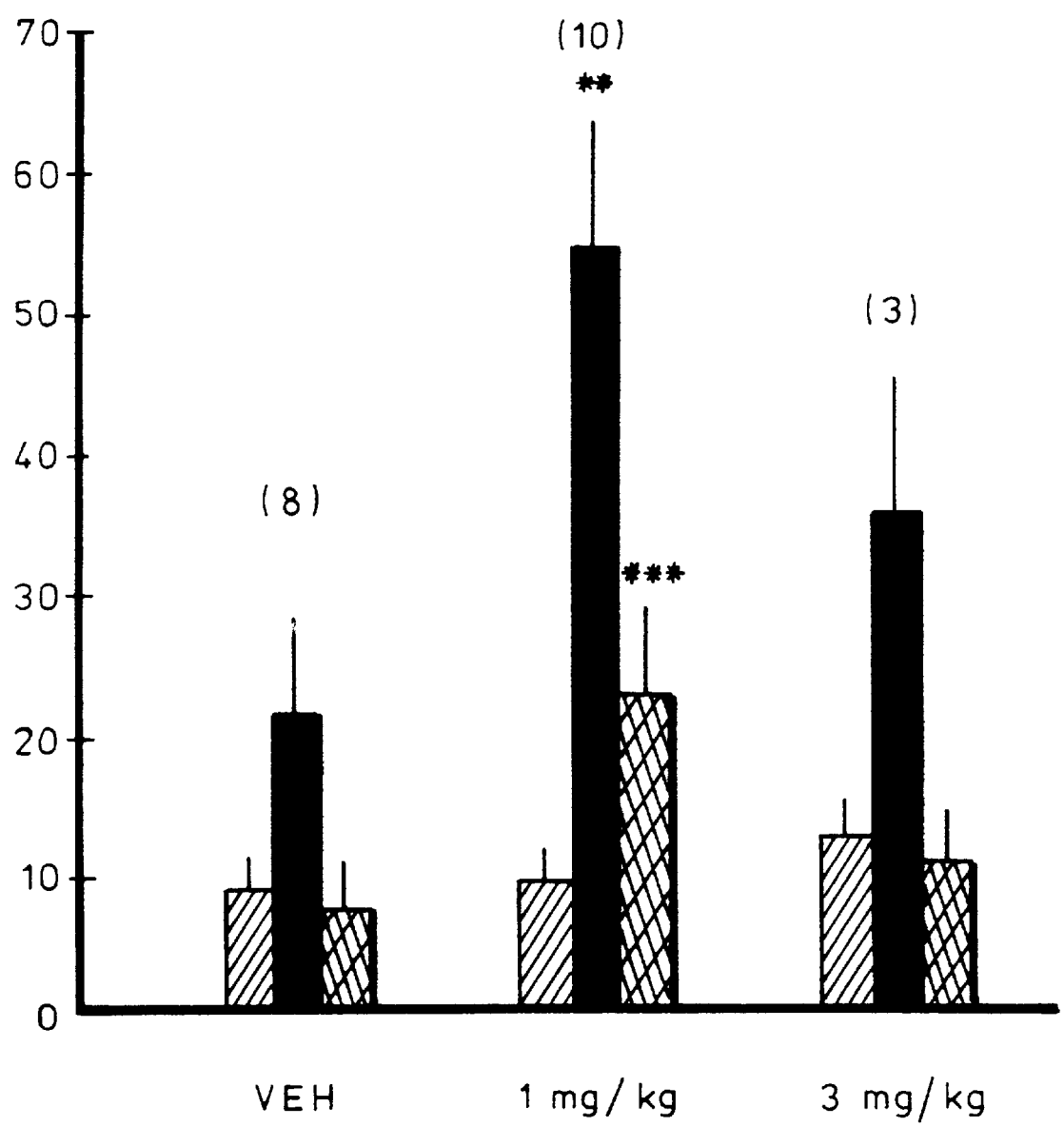
FIG. 11 is a graph illustrating test results of mice given a five minute test in the elevated plus-maze, twenty minutes after i.p. injection with 2'-chlorinated chrysin.
Figure 12:
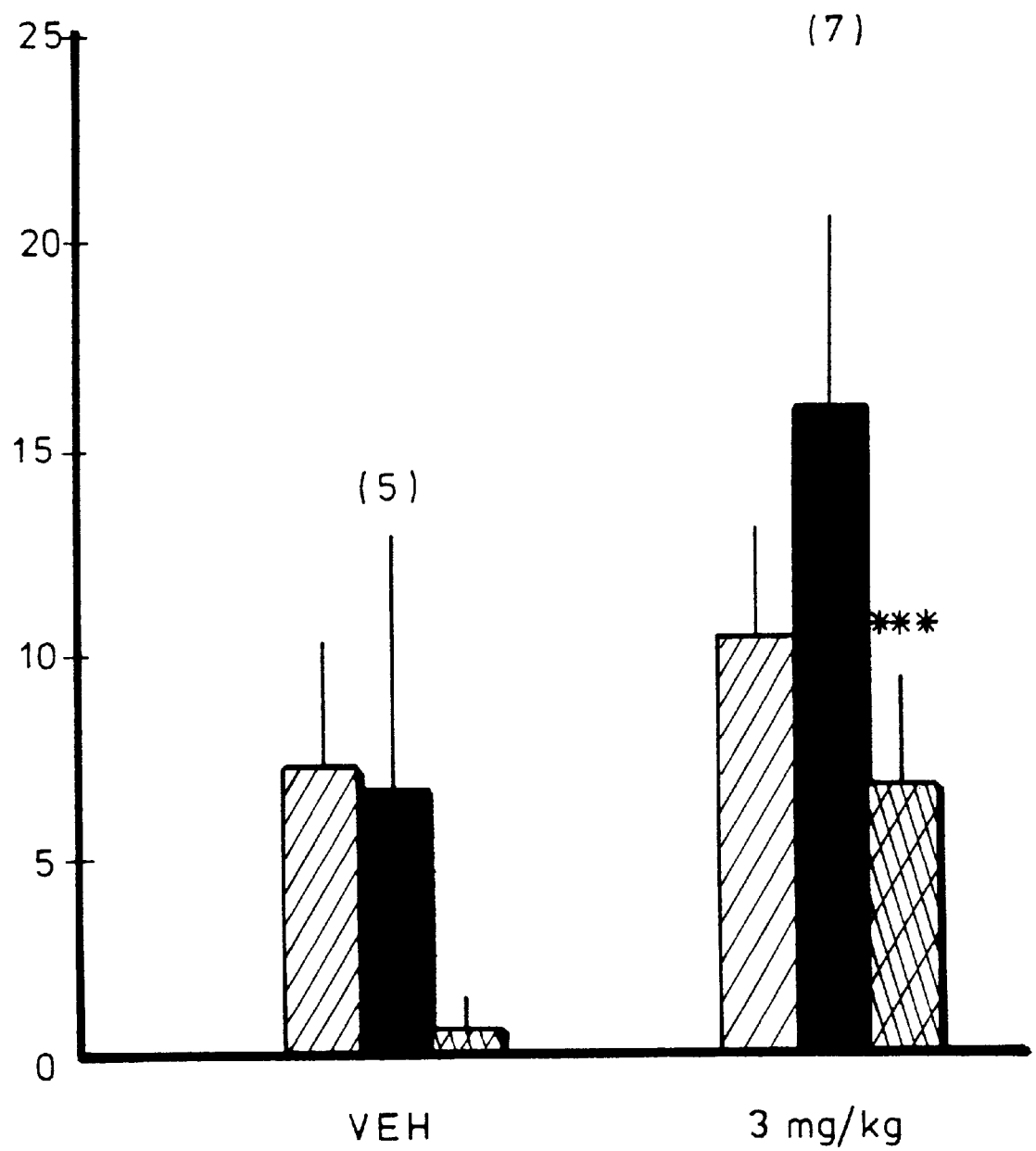
FIG. 12 is a graph illustrating test results of mice given a five minute test in the elevated plus-maze, twenty minutes after i.p. injection with 2'-fluorinated chrysin.
Figure 13:
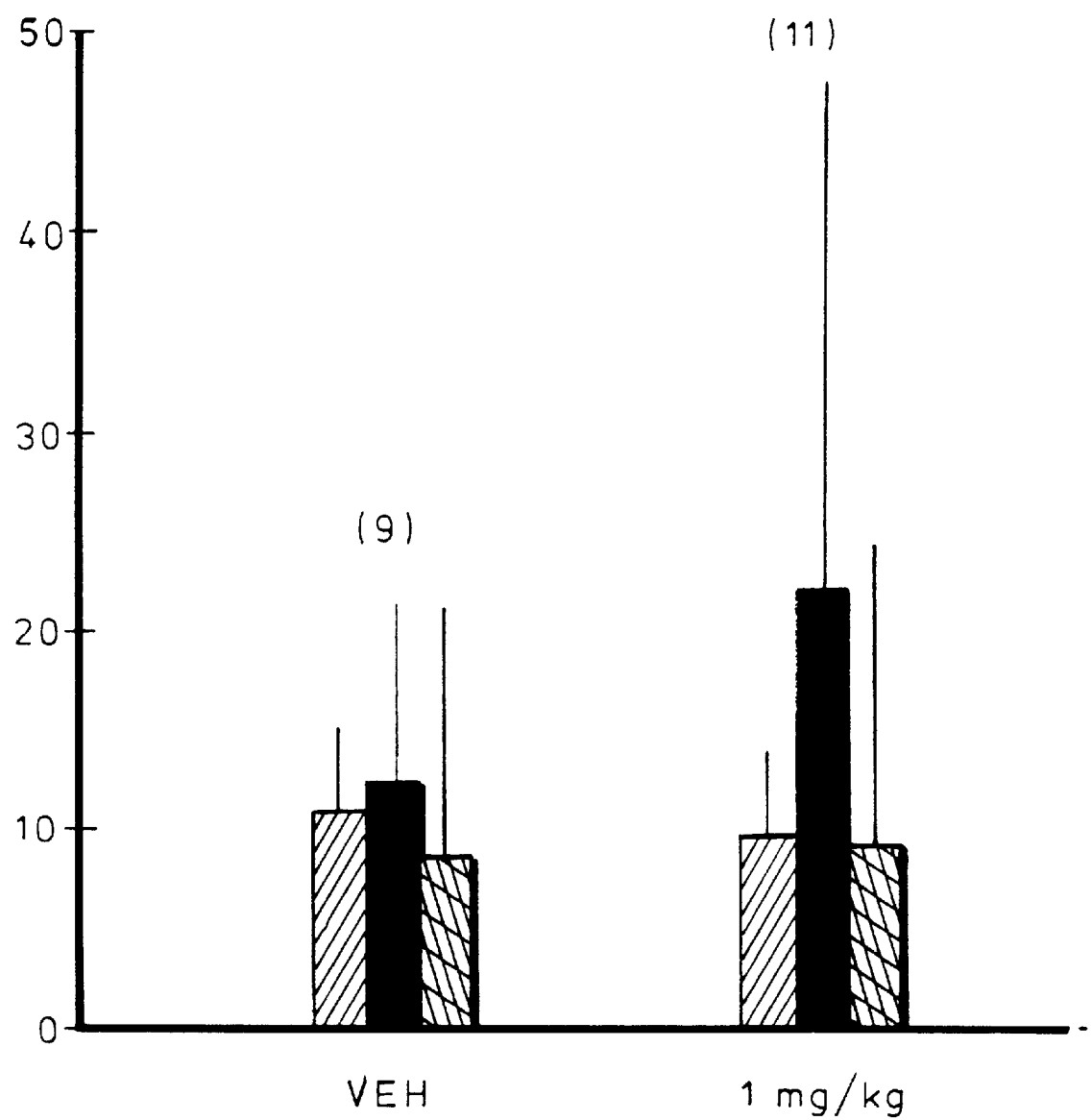
FIG. 13 is a graph illustrating test results of mice given a five minute test in the elevated plus-maze, twenty minutes after i.p. injection with 6,8-dibromochrysin.
Figure 14:
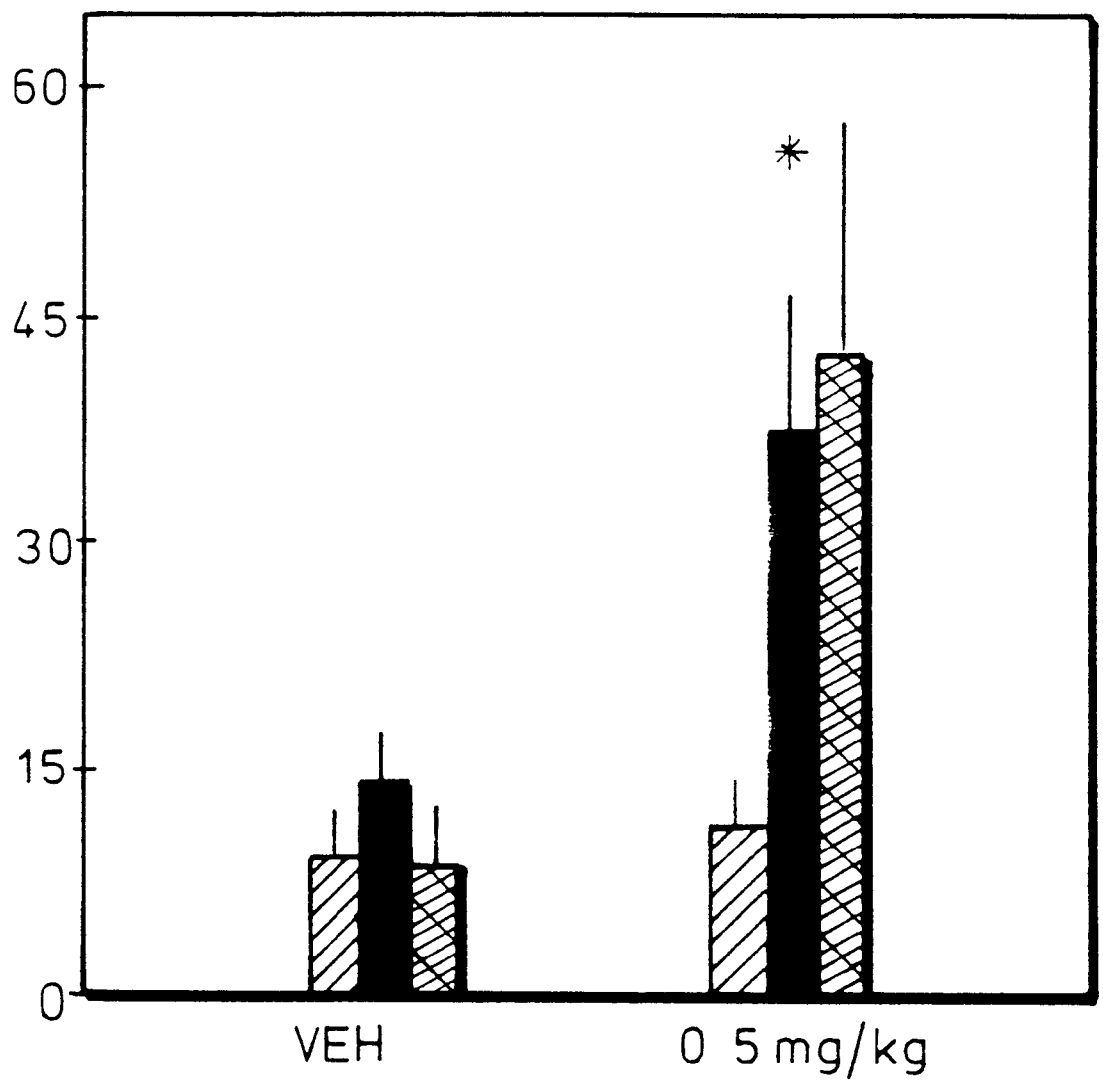
FIG. 14 is graph illustrating test results of mice given a five minute test in the elevated plus-maze, twenty minutes after i.p. injection with 7-bromoflavone.

FIGS. 10, 11, 12, 13 and 14 show mean (±S.E.M.) of total entries (hatched box), percentage of open arm entries (closed box) and percentage of time (sec) spent in the open arms (cross hatched box) in mice given a 5 min. test in the elevated plus-maze, 20 min. after i.p. injection with vehicle and a mixture of brominated flavone (0.6, 1,3 mg/kg) in FIG. 10; 2' chlorinated chrysin (1,3 mg/kg) in FIG. 11 and 2' fluorinated chrysin (3 mg/kg) in FIG. 12; 6, 8 dibromo chrysin (1 mg/kg) in FIG. 13; 7-bromo flavone (0.5 mg/kg) in FIG. 14. * p<0.01,  p<0.02, * p<0.05, significantly different from the controls (student's t-test after analysis of variance).

Figure 15:
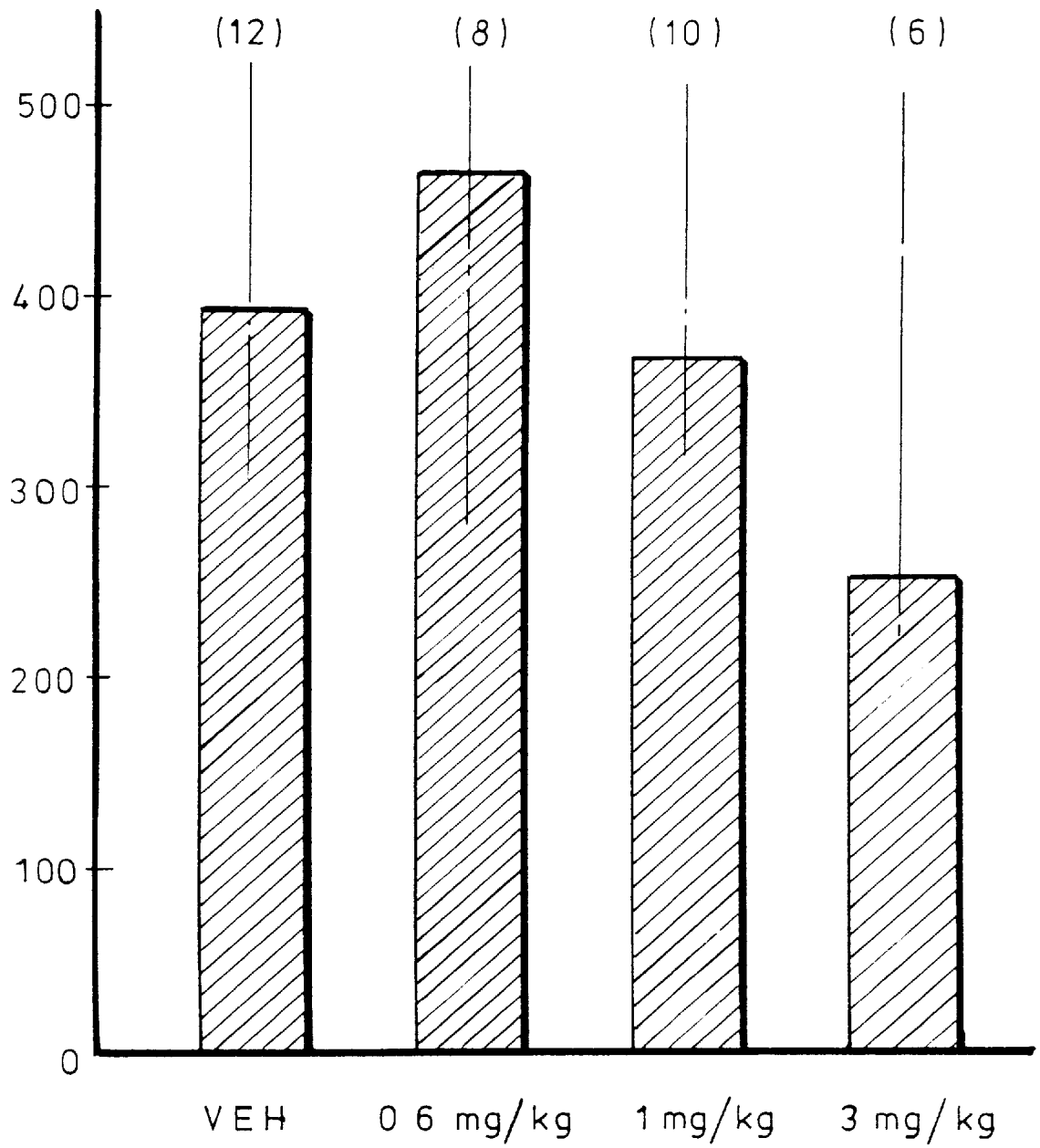
FIG. 15 is a graph illustrating ambulatory locomotor activity counts in mice during a five minute test session, twenty minutes after i.p. injection with a mixture of brominated flavones.
Figure 16:
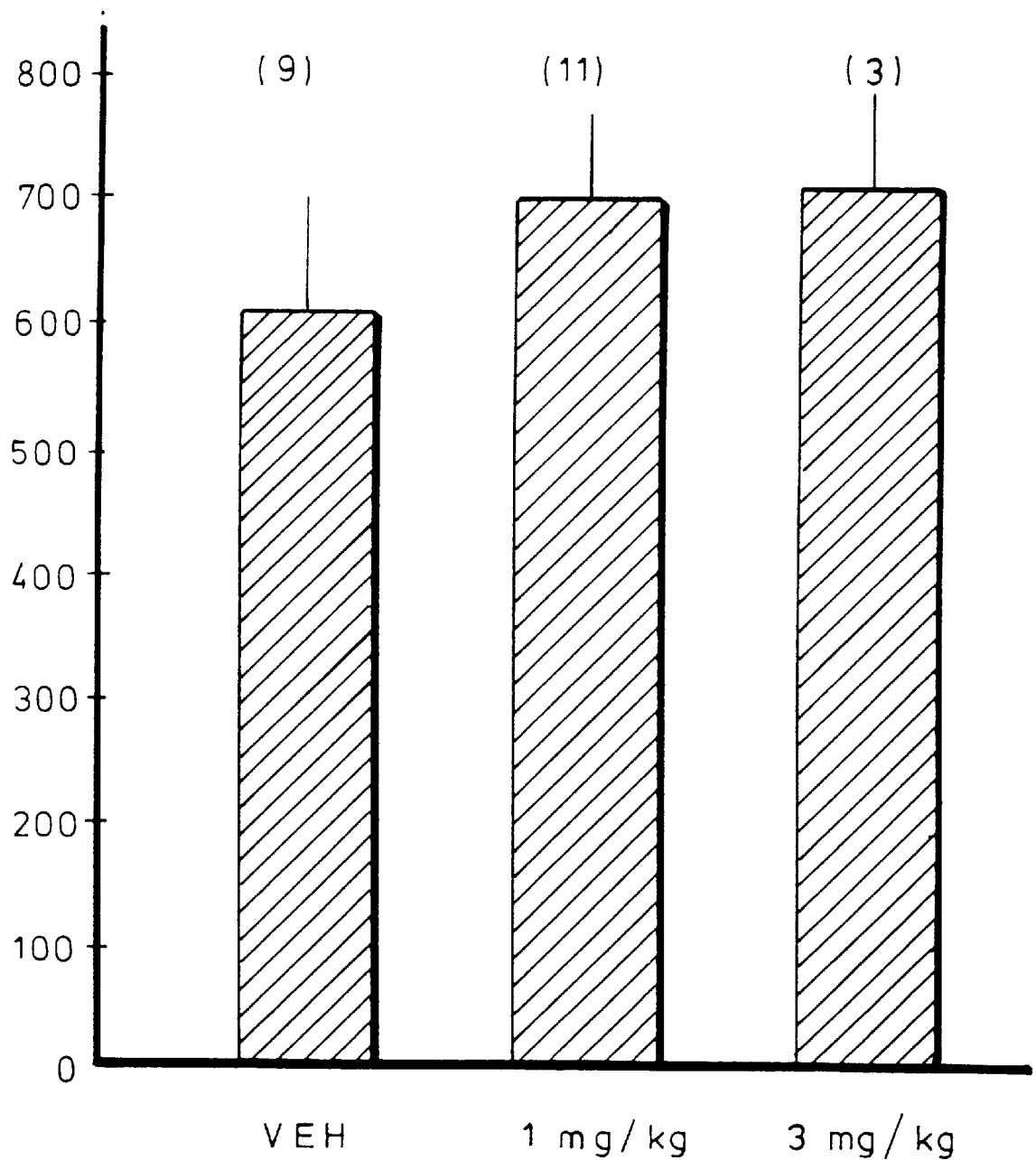
FIG. 16 is a graph illustrating ambulatory locomotor activity in mice during a five minute test session, twenty minutes after i.p. injection with a mixture of 2'-chlorinated chrysin.
Figure 17:
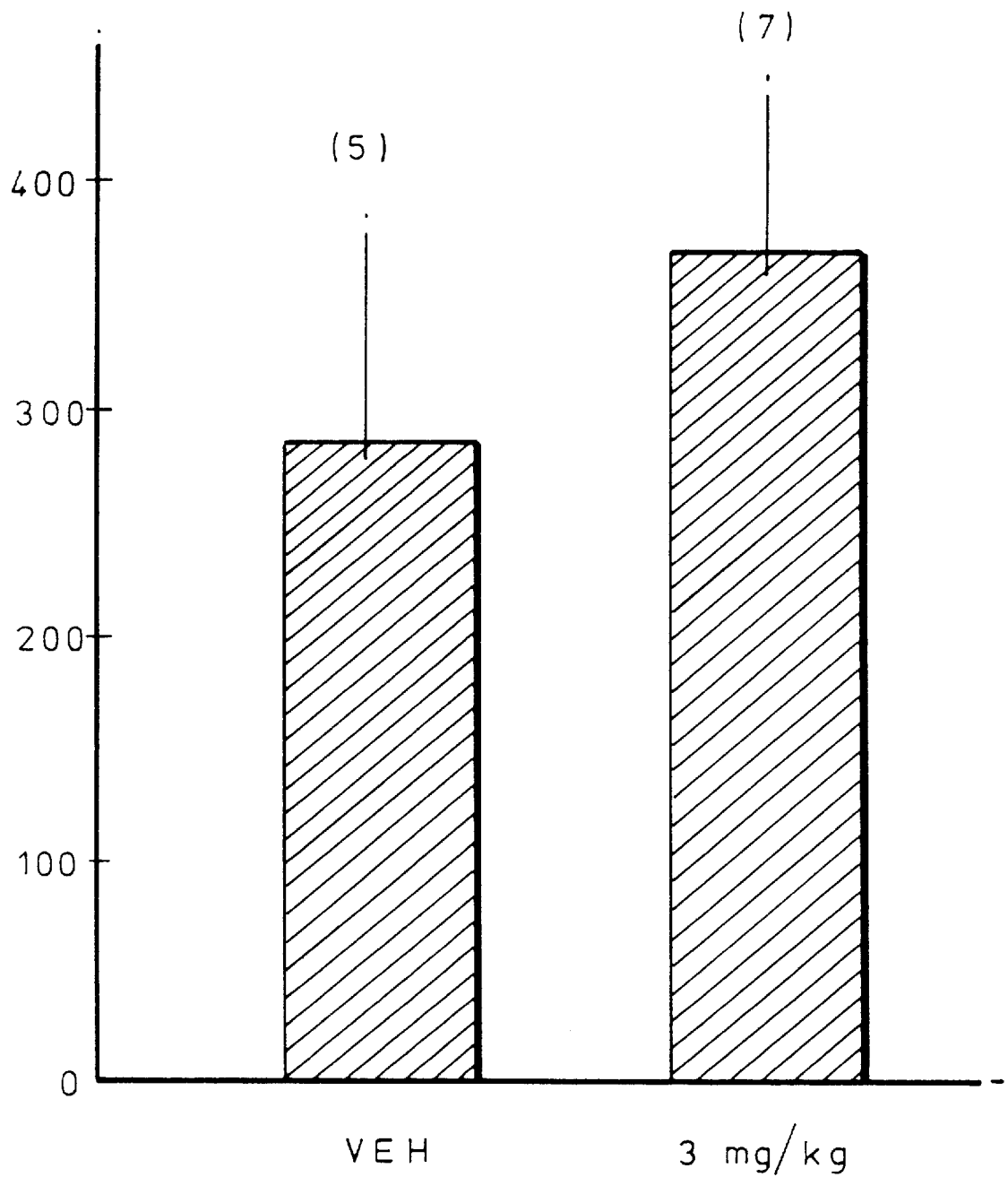
FIG. 17 is a graph illustrating ambulatory locomotor activity in mice during a five minute test session, twenty minutes after i.p. injection with a mixture of 2'-fluorinated chrysin.
Figure 18:
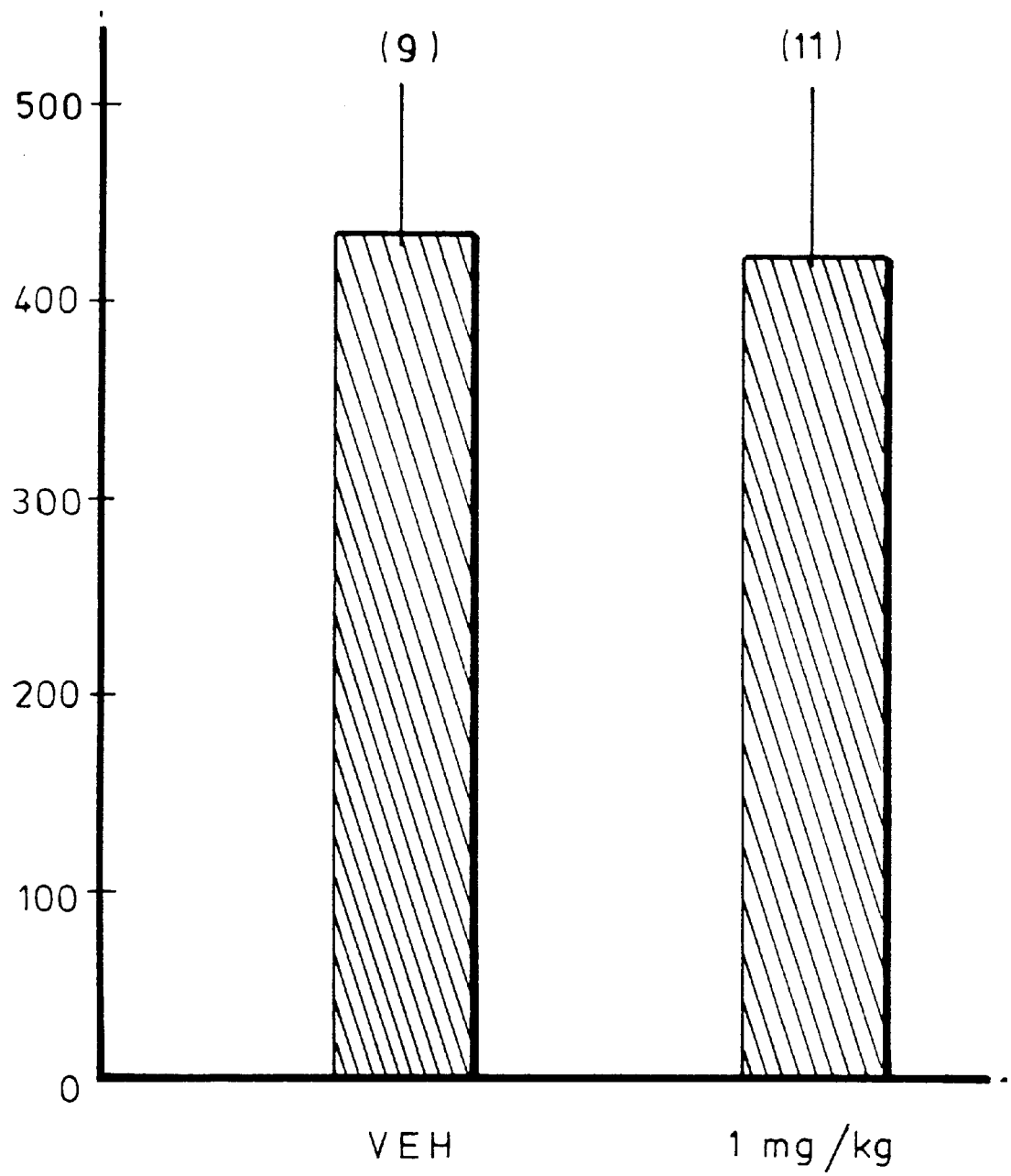
FIG. 18 is a graph illustrating ambulatory locomotor activity in mice during a five minute test session, twenty minutes after i.p. injection with a mixture of 6,8-dibromoflavin.

FIGS. 15, 16, 17 and 18 show ambulatory locomoter activity counts during a 5 min. test session in an OPTO-Varimex apparatus, 20 min. after i.p. injection with a mixture of brominated flavones (0.6,1,3 mg/kg), FIG. 15; 2' chlorinated chrysin (1,3 mg/kg); FIG. 16; 2' fluorinated chrysin (3 mg/kg), FIG. 17; 6,8 dibromoflavone, FIG. 18. Data are expressed as medians (interquartile range) of (n) number of animals. No significant difference was observed in comparison to the controls (Mann Whitney test). No significant change was observed in ambulatory activity when 7-bromo flavone was compared against a control (data not shown).

In all the experiments, diazepam DZ (0.3–6 mg/kg) was used as reference drug. FIG. 1 shows the typical pharmacological profile of increasing locomotor activity by DZ. Similarly, there was a significant increase in locomotor activity with equipotent doses of chrysin (0.6–1 mg/kg). FIG. 2 shows the performance of mice following i.p. administration of vehicle, DZ or chrysin on the elevated plus maze. DZ (0.3 and 0.6 mg/kg) increased the percentage of entries in the open arms (p<0.01) and the percentage of the time spent on the open arms (p<0.01). Chrysin (1 mg/kg) produced also an increase in both parameters (p<0.01). No differences were observed in the total arm entries (Table 1). Thus both DZ and CHRY displayed an anxiolytic effect. The effect of chrysin (1 mg/kg) on the number of entries into and the time spent on the open arms was prevented by the prior administration of Ro 15-1788, a central BZD receptor antagonist (FIG. 3).

As shown in FIG. 4 in the holeboard DZ (0.3 mg/kg) increased the number of head-dips (p<0.05) and at 1 mg/kg increased the time spent head-dipping (p<0.01). As expected, DZ (6 mg/kg) induced a decrease in both the number of head-dips and in the time spent head-dipping (p<0.01) which indicates sedation.

Chrysin (3 mg/kg) produced a significant increase in the time spent head-dipping but did not elicit sedative effects at high doses (10 mg/kg).

FIG. 5 shows that at 6 mg/kg DZ significantly decreased the percentage of animals grasping the horizontal wire, indicating a muscle relaxant effect. On the other hand, chrysin (0.6–30 mg/kg) was ineffective in the same test and produced no muscle relaxant effect.

Thus, chrysin had anxiolytic effects in the elevated plus maze test but did not exhibit sedation or muscle relaxation.

FIGS. 6 and 7 show analogous results for apigenin (API.) Apigenin administered interperitonealy shows anxiolytic effects in the elevated plus maze test (FIG. 6); but did not induce any effect in the holeboard test (FIG. 7) or the horizontal wire test (FIG. 7) indicating no sedative or muscle relaxant activity.

FIG. 8 shows that both chrysin and apigenin dampened the noradrenaline decrease in the locus coeruleus provoked by immobilisation stress. In comparison to diazepam, apigenin showed the most potent effect.

The figure shows percent change (related to controls) of locus coeruleus noradrenaline levels after stress and different treatment (as indicated in the figure). Rats were submitted to a 90-minute immobilization stress session in a plastic cylinder. The locus coeruleus was dissected out after killing by decapitation and noradrenaline assessed by HPLC with electrochemical detection. Doses were 1 mg/kg for each substance, injected i.p., 30 minutes before the stress session.

FIG. 9 shows the performance of mice following i.p. administration of vehicle, D2 or flavone on the elevated plus-maze. Flavone (1 mg/kg) increased the percentage of entries and time spent in the open arms (p<0.002) Mann-Whitney test.

FIG. 10 shows that at a concentration of 1 mg/kg a mixture of brominated flavones results in a significant increase in the number of entries into the open arms in comparison to the control. The corresponding ambulatory locomotion test (FIG. 14) shows no significant decrease in activity. Thus, the increased entries in the elevated plus-maze test show a reduction in anxiety without a significant decrease in activity (i.e. without a significant sedative effect).

A similar effect can be seen for 1 mg/kg administered 2' chlorinated chrysin (FIGS. 11 & 16), for 3 mg/kg administered 2' fluorinated chrysin (FIGS. 12 & 17), for 1 mg/kg administered 6,8 dibromo chrysin (FIGS. 13 & 18) and for 0.5 mg/kg administered 7-bromo flavone (FIG. 14).

EXAMPLE 3 (Competitive inhibition of $H^3$-flunitrazepam to benzodiazepine receptor)

This experiment was carried out as a general screen for compounds exhibiting benzodiazepine-like activity, in order to identify compounds for testing for specific anxiolytic activity.

Binding of 3H-flunitrazepam (0.7 nM) to the benzodiazepine receptor was carried out in extensively washed cerebral cortical membranes.

$H^3$-flunitrazepam has a Ki of 3 micromole to the benzodiazepine receptor.

$IC_{50}$ values were obtained using flavonoids at different concentrations ($10^{-10}$ to $10^{-3}$M).

Table II shows the results of the tests. Flavone, chrysin, apigenin and 6,8 dibromochrysin ($IC_{50}$=0.7–3 um) show benzodiazepine ligand behaviour similar to that of $^3$H-flunitrazepam. 7-bromo flavone and amentaflavone show a far higher affinity for the benzodiazepine receptor ($IC_{50}$= 0.05 um and 0.01 um respectively) than $^3$H-flunitrazepam.

The other flavonoids show weak benzodiazepine ligand behaviour.

EXAMPLE 4 (Induced seizures in mice)

Benzodiazepines in general show an anxiolytic effect, a sedative effect and an anticonvulsant effect. In order to assess the present compounds for anticonvulsant activity the following experiment was carried out.

The method of Medina et al Biochem.Pharm. 40 p2227–2231, (1990) was followed (with the exception that injections were carried out intraperitoneally) and the mice observed for seizures.

Table III shows that apigenin has no anticonvulsant activity. This differs from the benzodiazepines and shows that the flavonoids have a more selective and specific mode of action, being limited to anxiolytic activity.

TABLE I

Total number of arm entries made by mice during 5 min test in the elevated plus-maze, 20 min after drug injection.

|  | DRUGS (mg/kg) | n | TOTAL ARM ENTRIES |
|---|---|---|---|
| VEH |  | (53) | 8.7 ± 0.6 |
| DZ | 0.3 | (21) | 10.5 ± 0.8 |
|  | 0.6 | (22) | 12.4 ± 1.9 |
| CHRYSIN | 1 | (36) | 9.9 ± 0.8 |
|  | 3 | (21) | 8.7 ± 1.1 |
|  | 10 | (15) | 10.2 ± 1.1 |

Data are expressed as means ± S.E.M. of n = number of animals.
Analysis of variance F(5,160) = 2.27, p < 0.05

TABLE II

Structure - activity relationships of several flavonoids on the $^3$H Flunitrazepam binding to bovine brain membranes.

| FLAVONOID | $^3$H Flunitrazepam binding $IC_{50}$ (uM) |
|---|---|
| Flavone | 1 |
| Apigenin | 3 |
| Isoquercetin | 10 |
| 6,8 dibromochrysin | 0.7 |
| Isoquercitrin | 80 |
| 5 hydroxy 7 methoxyflavone | 46 |
| Rutin | 60 |
| 2' fluorochrysin | 8 |
| 2' chlorochrysin | 9 |
| chrysin | 2 |
| flavanone | 40 |
| 7-bromoflavone | 0.05 |
| Amentoflavone | 0.01 |
| Ginkgetin | 5 |
| Isoginkgetin | 4–5 |

TABLE III

EFFECTS OF IP ADMINISTRATION OF APIGENIN ON PTZ INDUCED SEIZURES IN MICE.

| Doses (mg/kg) | Number of animals with clonic convulsions |
|---|---|
| PTZ | 31/31 |
| Diazepam 3 + PTZ | 0/6 |
| Apigenin 3 + PTZ | 8/8 |
| Apigenin 20 + PTZ | 3/3 |
| Apigenin 40 + PTZ | 12/14 |
| Apigenin 80 + PTZ | 11/11 |

The convulsant doses of pentylenetetrazole are between 50–80 mg/kg in different experiments carried out in 6 independent days.

5,7-Dihydroxy-2'-fluoroflavone (2'-fluorochrysin). Light tan prisms, mp 273–276° C. $^1$H NMR δ (DMSO-$d_6$) 6.24 (1H,d, J=1.8 Hz, H-6), 6.47 (1H,d, J=1.8 Hz, H-8), 6.69 (1H,s,H-3), 7.44 (2H,m,H-3'/-6'), 7.67 (1H,ddd, J=6.1, J''=1.3 Hz,H-4' or -5'), 7.98 (1H,ddd, J=J'=7.4, J''=1.2 Hz, H-5' or -4'), 12.67

(1H, s, C-5-OH). $^{13}$C NMR δ (DMSO-d$_6$) 94.29(C-8), 99.33(C-6), 104.05 (C-4a), 109.84 (d, J=10.6 Hz. C-3), 117.10 (d, J=21.9 Hz, C-6'), 119.38 (d, J=10.6 Hz, C-1'), 125.42 (d, J=3.8 Hz, C-3'), 129.72 (C-5' or -4'), 134.05 (d, J=36 Hz, C-4' or 5'), 157.72 (C-8a), 158.71 (d, J=75 Hz, C-2'), 159.21 (C-2), 161.60(C-5), 164.82(C-7), 181.63(C-4).

5,7-Dihydroxy-2'-chloroflavone(2'-chlorochrysin). Yellow granular powder, sublimes from 225° C. melts 273–275° C. $^1$H NMR δ (DMSO-d$_6$) 6.35 (1H, d, J=1.8 Hz, H-6), 6.50 (1H, d, J=1.8 Hz, H-8), 6.66(1H, s, H-3), 7.63 (1H, ddd, J=J'=7.5, J"=1.3 Hz, H-5' or 4'), 7.70 (1H, ddd, J=J'=7.6, J"=1.3 Hz, H4' or 5'), 7.76 (1H, dd, J=7.8, J'=1.0 Hz H-6' or -3'), 7.78 (1H, dd, J=7.4, J'=1.2 Hz, H-3' or -6'), 12.67 (1H, s, C-5-OH). $^{13}$C NMR δ (DMSO-d$_6$) 94.35 (C-8), 99.54 (C-6), 103.96 (C-4a), 110.76 (C-3), 127.97 (C-5' or 4'), 130.69 (C-6' or 3'), 131.13 (C-1), 131.50 (C-3' or 6'), 131.81 (C-2'), 132.88 (C-4' or -5'), 158.02 (C-8a), 161.75 (C-5), 162.86 (C-7), 165.26 (C-2), 181.58 (C-4).

6,8-Dibromo-5,7-dihydroxyflavone (6,8-dibromochrysin). Prepared by bromination of chrysin at room temperature with excess bromine in acetic acid. Very fine, light yellow needles, subliming from 265° C. to give prisms, mp (309) 320° C., 1H NMR δ (DMSO-d$_6$) 7.17 (s, H-3), 7.59 (dd. J=J'=6.5 Hz, H-3'/5'), 7.62 (dd, J=J'=6.5 Hz, H4'), 8.12 (d, J=6.4 Hz, H-2'/6'), 13.71 (s, C-5-OH). $^{13}$C NMR δ (DMSO-d$_6$) 88.37 (C-8), 94.47 (C-6), 105.03 (C-4a), 126.0 (C-3), 126.37 (C-2'/6'), 129.14 (C-3'/5'), 130.13 (C-1'), 132.35 (C4'), 152.18 (C-7), 156.97 (C-8a or -5), 157.34 (C-5 or 8a), 163.41 (C-2), 181.44 (C-4).

Tectochrysin (5-hydroxy-7-methoxyflavone). Prepared from chrysin by warming with one equivalent of dimethyl sulphate in DMF with fine ground K$_2$CO$_3$. Fine, light yellow needles, mp 175–180 ° C. (lit. 163° C.). $^1$H NMR δ (DMSO-d$_6$) 3.87 (s,OCH$_3$), 6.39 (d. J=1.7 Hz, H-6), 6.80 (d, J=1.7 Hz, H-8), 7.02 (s,H-3), 7.58 (dd, J=J'=7.8 Hz. H-3'/5'), 7.60 (tt, J≈7.8 Hz, H-4'), 8.09 (d,J=7.8 Hz, H-2'/6') 12.80 (s, C-5-OH).

5,7-Dimethoxyflavone (chrysin 5,7-di-O-methyl ether). Prepared similarly to the previous compound, but with excess dimethyl sulphate. Light tan powder, mp 147–149° C. $^1$H NMR δ (CDCl$_3$) 3.91 (s,OCH$_3$), 3.96 (s,OCH$_3$), 6.37 (d, J=2.0 Hz. H-6), 6.57 (d, J=2.2 Hz, H-8), 6.68 (s, H-3), 7.50 (dd, H-3'/5'), 7.51 (tt, H4'), 7.87 (d, J=5.3 Hz?, H-2'/6').

2'-Chloro-5-hydroxy-7-methoxyflavone (2'-chlorotectochrysin). Prepared from 2'-chlorochrysin by warming with one equivalent of dimethyl sulphate in DMF with finely ground K$_2$CO$_3$. Light yellow needles, sublimes from 160° C., melts 183–185° C. $^1$H NMR δ (DMSO-d$_6$). 3.88 (s,OCH$_3$), 6.47 (br s, H-6), 6.66 (s, H-3), 6.72 (br s, H-8), 7.6 (m, H-3'/4'/5'), 7.82 (br d, J≈6.9 Hz, H-6'), 12.64 (s, C-5-OH).

2'-Chloro-6,8-dibromo-5,7-dihydroxyflavone (2'-chloro-6,8-dibromochrysin). Prepared from 2'-chlorochrysin by bromination with excess bromine in acetic acid. Very fine, pale yellow needles, sublimes from 250° C. melts 285–290° C. $^1$H NMR δ (DMSO-d$_6$) 6.83 (s, H-3), 7.6 (3H, m, H-3'/4'/5'), 7.84 (d, J=6.2 Hz, H-6'), 13.59 (s, C-5-OH). $^{13}$C NMR 6 (DMSO-d$_6$) 88.66 (C-8), 94.97 (C-6) 105.20 (C-4a), 111.02 (C-3), 128.02 (C-5'), 130.50 (C-6'), 130.90 (C-1'), 131.72 (C-3'), 131.91 (C-4'), 133.24 (C-2'), 152.99 (C-7), 157.26 (C-8a or -5), 157.88 (C-5 or -8a), 163.30 (C-2), 181.40 (C-4).

We claim:

1. A flavonoid compound 6,8-dibromochrysin.
2. A pharmaceutical formulation which comprises a flavonoid compound of general Formula (I):

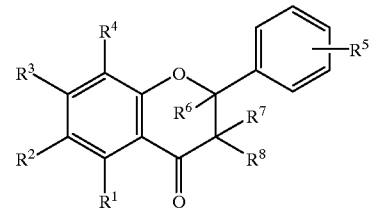

in admixture with a pharmaceutically acceptable carrier, wherein:

$R^1$, $R^3$, and $R^8$ are independently selected from the group consisting of H, OH, and halo;

$R^2$ and $R^4$ are both halo;

$R_5$ is selected from the group consisting of H and OH; and $R^6$ and $R^7$ together form a single bond, with the proviso that:

(i) when $R^1$ is H, then $R^3$ is not halo;
(ii) when $R^1$ is Cl or I, then $R^3$ is not H;
(iii) when $R^1$ is OH, then $R^3$ is not H; and
(iv) when $R^1$ is H, then $R^5$ is not H.

3. A pharmaceutical formulation comprising the flavonoid compound 6,8-dibromochrysin in admixture with a pharmaceutically acceptable carrier.

* * * * *

UNITED STATES PATENT AND TRADEMARK OFFICE
CERTIFICATE OF CORRECTION

PATENT NO. : 6,004,998

DATED : December 21, 1999

INVENTOR(S) : Cassels et al.

It is certified that error appears in the above-identified patent and that said Letters Patent is hereby corrected as shown below:

In the References Cited, OTHER PUBLICATIONS, line 4, "Occuring" should read --Occurring--.

Column 12, line 36, "$R_5$" should read --$R^5$--.

Signed and Sealed this

Nineteenth Day of September, 2000

Attest:

Q. TODD DICKINSON

*Attesting Officer*          *Director of Patents and Trademarks*